(12) United States Patent
Besner et al.

(10) Patent No.: US 12,383,656 B2
(45) Date of Patent: Aug. 12, 2025

(54) TISSUE ENGINEERED INTESTINE

(71) Applicants: Research Institute at Nationwide Children's Hospital, Inc., Columbus, OH (US); Nanofiber Solutions LLC, Columbus, OH (US)

(72) Inventors: Gail E. Besner, Dublin, OH (US); Yanchun Liu, Columbus, OH (US); Jed Johnson, Columbus, OH (US)

(73) Assignees: Research Institute at Nationwide Children's Hospital, Inc., Columbus, OH (US); Nanofiber Solutions LLC, Columbus, OH (US)

( * ) Notice: Subject to any disclaimer, the term of this patent is extended or adjusted under 35 U.S.C. 154(b) by 1312 days.

(21) Appl. No.: 16/728,863

(22) Filed: Dec. 27, 2019

(65) Prior Publication Data

US 2021/0030924 A1 Feb. 4, 2021

Related U.S. Application Data

(63) Continuation of application No. 14/774,045, filed as application No. PCT/US2014/028186 on Mar. 14, 2014, now abandoned.

(60) Provisional application No. 61/783,655, filed on Mar. 14, 2013.

(51) Int. Cl.
| | |
|---|---|
| *A61L 27/38* | (2006.01) |
| *A61L 27/18* | (2006.01) |
| *A61L 27/22* | (2006.01) |
| *A61L 27/56* | (2006.01) |

(52) U.S. Cl.
CPC .......... *A61L 27/3882* (2013.01); *A61L 27/18* (2013.01); *A61L 27/227* (2013.01); *A61L 27/38* (2013.01); *A61L 27/3826* (2013.01); *A61L 27/383* (2013.01); *A61L 27/3873* (2013.01); *A61L 27/3886* (2013.01); *A61L 27/3891* (2013.01); *A61L 27/3895* (2013.01); *A61L 27/56* (2013.01); *A61L 2400/12* (2013.01); *A61L 2430/22* (2013.01)

(58) Field of Classification Search
None
See application file for complete search history.

(56) References Cited

U.S. PATENT DOCUMENTS

| | | |
|---|---|---|
| 4,505,266 A | 3/1985 | Yannas et al. |
| 5,190,878 A | 3/1993 | Wilhelm |
| 5,231,169 A | 7/1993 | Constantz et al. |
| 5,605,835 A | 2/1997 | Hu et al. |
| 5,688,687 A | 11/1997 | Palsson et al. |
| 5,811,393 A | 9/1998 | Klagsbrun et al. |
| 5,888,807 A | 3/1999 | Palsson et al. |
| 5,985,653 A | 11/1999 | Armstrong et al. |
| 6,001,642 A | 12/1999 | Tsao |
| 6,090,622 A | 7/2000 | Gearhart et al. |
| 6,096,532 A | 8/2000 | Armstrong et al. |
| 6,191,109 B1 | 2/2001 | Besner et al. |
| 6,387,878 B1 | 5/2002 | Besner et al. |
| 7,276,479 B2 | 10/2007 | Besner et al. |
| 7,361,638 B2 | 4/2008 | Berlanga Acosta et al. |
| 7,456,151 B2 | 11/2008 | Li et al. |
| 8,093,213 B2 | 1/2012 | Besner et al. |
| 9,060,977 B2 | 6/2015 | Besner et al. |
| 2003/0129751 A1 | 7/2003 | Grikscheit et al. |
| 2013/0130984 A1 | 5/2013 | Besner |
| 2013/0216502 A1 | 8/2013 | Besner |
| 2013/0244935 A1 | 9/2013 | Besner |
| 2015/0030657 A1 | 1/2015 | Ludlow et al. |

FOREIGN PATENT DOCUMENTS

| | | |
|---|---|---|
| WO | WO-1992/006705 A1 | 4/1992 |
| WO | WO-2000/069449 | 11/2000 |
| WO | WO-2008/134635 A1 | 11/2008 |
| WO | WO-2011/134957 A1 | 11/2011 |
| WO | WO-2013/052712 A2 | 4/2013 |
| WO | WO-2013/150303 A1 | 10/2013 |

OTHER PUBLICATIONS

Baghaban et al., Mesenchymal stem cells from murine amniotic fluid as a model for preclinical investigation, Arch. Iran. Med., 14(2):96-103 (2011).

Baksh et al., Adult mesenchymal stem cells: characterization, differentiation, and application in cell and gene therapy, J. Cell. Mol. Med., 8(3):301-16 (2004).

Barker et al., Identification of stem cells in small intestine and colon by marker gene Lgr5, Nature, 449:1003-7 (2007).

Barker et al., Tracking down the stem cells of the intestine: strategies to identify adult stem cells, Gastroenterology, 133:1755-60 (2007).

Besner et al., Interaction of heparin-binding EGF-like growth factor (HB-EGF) with the epidermal growth factor receptor: Modulation by heparin, heparinase, or synthetic heparin-binding HB-EGF fragments, Growth Factors, 7:289-96 (1992).

Bongso et al., Improved quality of human embryos when co-cultured with human ampullary cells, Hum. Reprod., 4:706 (1989).

Chen et al., Heparin-binding EGF-like growth factor protects intestinal stem cells from injury in a rat model of necrotizing enterocolitis, Lab. Invest., 92:331-44 (2012).

Chen et al., Intestinal phenotype in mice overexpressing a heparin-binding EGF-like growth factor transgene in enterocytes, Growth Factors, 28:82-97 (2010).

Choi et al., Central emboli rather than saddle emboli predict adverse outcomes in patients with acute pulmonary embolism, J. Pediatric Surg., 33:991-6 (1998).

(Continued)

*Primary Examiner* — Nannette Holloman
(74) *Attorney, Agent, or Firm* — MARSHALL, GERSTEIN & BORUN LLP

(57) ABSTRACT

The invention provides for engineered intestinal construct and methods of making these constructs. The invention also provides for methods of treating short bowel syndrome or methods of repairing an intestine after resection comprising inserting an engineered intestinal construct into the intestine of a subject in need.

8 Claims, 16 Drawing Sheets

Specification includes a Sequence Listing.

(56) References Cited

OTHER PUBLICATIONS

Dexter et al., Conditions controlling the proliferation of haemopoietic stem cells in vitro, J. Cell. Physiol., 91:335-44 (1977).
El-Assal et al., Heparin-binding EGF-like growth factor preserves mesenteric microcirculatory blood flow and protects against intestinal injury in rats subjected to hemorrhagic shock and resuscitation, Surgery, 142: 234-42 (2007).
El-Assal et al., Heparin-binding epidermal growth factor-like growth factor and intestinal ischemia-reperfusion injury, Semin. Pediatr. Surg., 13: 2-10 (2004).
Feng et al., Heparin-binding EGF-like growth factor (HB-EGF) and necrotizing enterocolitis, Semin. Pediatr. Surg., 14: 167-74 (2005).
Feng et al., Heparin-binding epidermal growth factor-like growth factor decreases the incidence of necrotizing enterocolitis in neonatal rats, J. Ped. Surg. 41: 144-9 (2006).
Friedenstein et al., Fibroblast precursors in normal and irradiated mouse hematopoietic organs. Exp. Hematol., 4, 267-74 (1976).
Gardner et al., Culture and transfer of human blastocysts increases implantation rates and reduces the need for multiple embryo transfers, Fertil. Steril., 69:84 (1998).
Greenberger, Sensitivity of corticosteroid-dependent insulin-resistant lipogenesis in marrow preadipocytes of obese-diabetic (db/db) mice, Nature, 275:7524 (1978).
Grikscheit et al., Tissue-engineered small intestine improves recovery after massive small bowel resection, Annals of surgery, 240:748-54 (2004).
Gui et al., Heregulin protects mesenchymal stem cells from serum deprivation and hypoxia-induced apoptosis, Mol. Cell. Biochem., 305(1-2):171-8 (2007).
Gupta et al., Tissue engineering of small intestine—current status, Biomacromolecules., 7:2701-9 (2006).
Hahn et al., Pre-treatment of mesenchymal stem cells with a combination of growth factors enhances gap junction formation, cytoprotective effect on cardiomyocytes, and therapeutic efficacy for myocardial infarction, J. Am. Coll. Cardiol., 51(9):933-43 (2008).
Higashiyama et al., A heparin-binding growth factor secreted by macrophage-like cells that is related to EGF, Science, 251:936-9 (1991).
Http://symptomsofulcerativecolitissupport.com/what-is-ulcerative-colitis/what-is the-colon/.
Hu et al., Transplantation of hypoxia-preconditioned mesenchymal stem cells improves infarcted heart function via enhanced survival of implanted cells and angiogenesis, J. Thorac. Cardiovasc. Surg., 135(4):799-808 (2008).
International Preliminary Report on Patentability, PCT/US2014/028186, dated Sep. 15, 2015.
International Search Report and Written Opinion of the International Search Authority, European Patent Office, PCT/US2014/028186, dated Oct. 14, 2014.
Jackson et al., Defective valvulogenesis in HB-EGF and TACE-null mice is associated with aberrant BMP signaling, EMBO J., 22: 2704-16 (2003).
Johnson et al., Electrospun PCL in vitro: a microstructural basis for mechanical property changes, J. Biomat. Sci. Polymer Ed., 20(4):467-81 (2009).
Johnson et al., Microstructure-Property relationships in a tissue-engineering scaffold, J. Appl. Polymer Sci., 104(5):2919-27 (2007).
Jwo et al., Intestinal regeneration by a novel surgical procedure, Br. J. Surg., 95:657-63 (2008).
Kassis et al., Isolation of mesenchymal stem cells from G-CSF-mobilized human peripheral blood using fibrin microbeads, Bone Marrow Transplant., 37(10):967-76 (2006).
Kawada et al., Nonhematopoietic mesenchymal stem cells can be mobilized and differentiate into cardiomyocytes after myocardial infarction, Blood, 104:3581-7 (2004).
Kern et al., Comparative analysis of mesenchymal stem cells from bone marrow, umbilical cord blood, or adipose tissue, Stem Cells, 24:1294-301 (2006).
Koda et al., Hematopoietic stem cell and marrow stromal cell for spinal cord injury in mice, Neuroreport, 16:1763-7 (2005).
Lannutti et al., Electrospinning for tissue engineering scaffolds, Mat. Sci. Engin, 27:504-9 (2007).
Lee et al., Biomed. Mater., 8(1): 0101201 (2012).
Lee et al., Isolation of neural stem cells from the postnatal cerebellum, Nat. Neurosci, 8:723-9 (2005).
Levin et al., Human tissue-engineered small intestine forms from postnatal progenitor cells, J. Pediatr. Surg. 48:129-37 (2013).
Liu et al., Angiopoietin-1 protects mesenchymal stem cells against serum deprivation and hypoxia-induced apoptosis through the PI3K/Akt pathway, Acta. Pharmacol. Sin. 29:815-22 (2008).
Liu et al., The efficacy of sublingual immunotherapy with Dermatophagoides farinae vaccine in a murine atopic dermatitis model, Acta. Pharmacol. Sin.,29(7):815-22 (2008).
Markel et al., Stem cells as a potential future treatment of pediatric intestinal disorders, J. Pediatr. Surg., 43:1953-63 (2008).
Martin et al., Timing, route, and dose of administration of heparin-binding epidermal growth factor-like growth factor in protections against intestinal ischemia-reperfusion injury, J. Ped. Surg. 40(11):1741-7 (2005).
Pasha et al., Preconditioning enhances cell survival and differentiation of stem cells during transplantation in infarcted myocardium, Cardiovasc. Res.,77(1):134-42 (2008).
Phinney et al., Plastic adherent stromal cells from the bone marrow of commonly used strains of inbred mice: variations in yield, growth, and differentiation, J. Cell. Biochem., 72(4):570-85 (1999).
Pillai et al., Heparin-binding epidermal growth factor-like growth factor protects rat intestine from ischemia/reperfusion, J. Surg. Res., 87(2): 225-31 (1999).
Pittenger et al., Multilineage potential of adult human mesenchymal stem cells, Science, 284(5411):143-7 (1999).
Potten et al., The stem cells of small intestinal crypts: where are they?, Cell. Prolif., 42:731-50 (2009).
Sangiorgi et al., Heparin-binding EGF-like growth factor protects intestinal stem cells from injury in a rat model of necrotizing enterocolitis, Nat. Genet. 40:915-20 (2008).
Sato et al., Single Lgr5 stem cells build crypt-villus structures in vitro without a mesenchymal niche, Nature, 459:262-5 (2009).
Scoville et al., Current view: intestinal stem cells and signaling, Gastroenterology, 136: 849-64 (2008).
Snippert et al., Prominin-1/CD133 marks stem cells and early progenitors in mouse small intestine, Gastroenterology, 136:2187-94 (2009).
Tayalia et al., Controlled growth factor delivery for tissue engineering, Adv. Mater. 21:3269-85 (2009).
Togel et al., Administered mesenchymal stem cells protect against ischemic acute renal failure through differentiation-independent mechanisms, Am. J. Physiol. Renal. Physiol., 289:F31-42 (2005).
Vaananen et al., Mesenchymal stem cells, Ann. Med., 37:469-79 (2005).
Warner, Tissue Engineered Small Intestine, Ann. Surg., 5(240):755-6 (2004).
Yang et al., Characterization of neural stem cells on electrospun poly(L-lactic acid) nanofibrous scaffold, J. Biomater. Sci. Polym. Ed. 15:1483-97 (2004).
Yu et al., Heparin-binding EGF-like growth factor protects pericytes from injury, J. Surg. Res., 172:165-76 (2012).
Zhang et al., Comparison of mesenchymal stem cells from human placenta and bone marrow, Chinese Med. J., 17 (6):882-887 (2004).
Zhang et al., Effects of transplanted bone marrow mesenchymal stem cells on the irradiated intestine of mice, J. Biomed. Sci., 2008;15:585-94.
Zhu et al., Prominin 1 marks intestinal stem cells that are susceptible to neoplastic transformation. Nature, 457: 603-607 (2009).

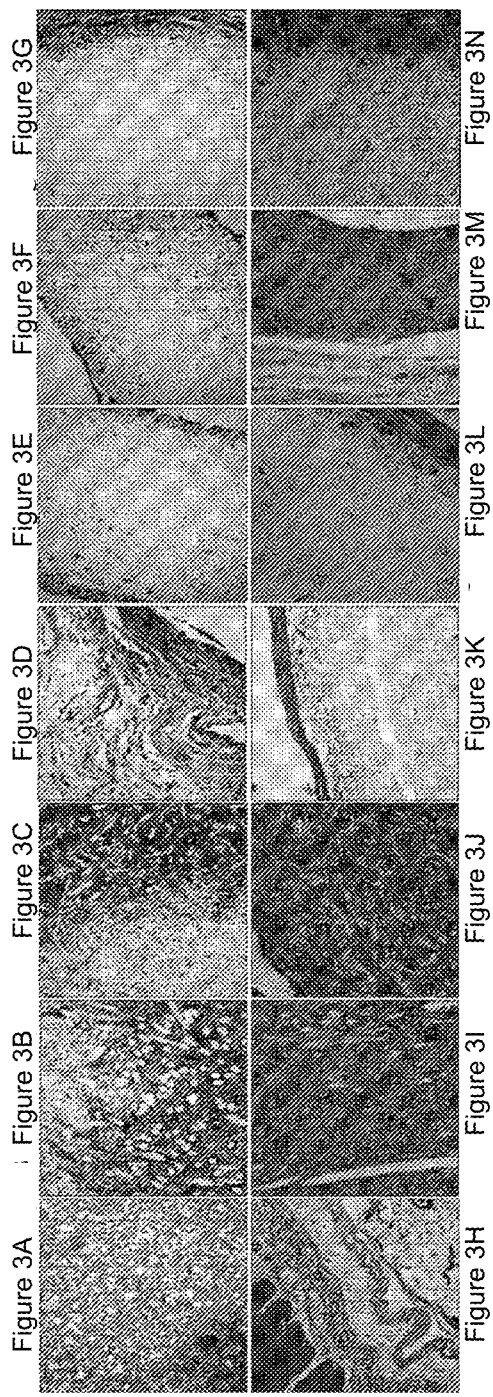

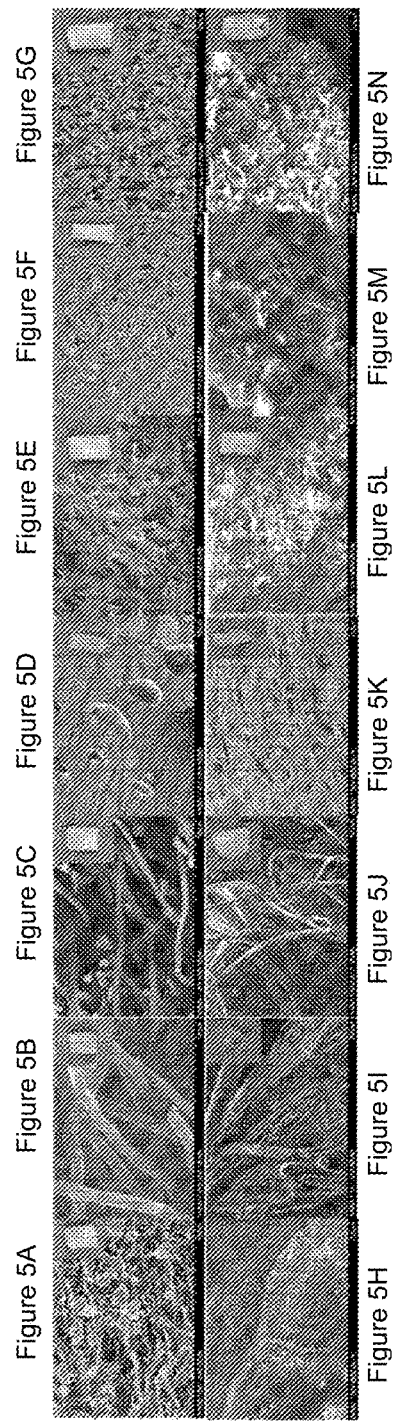

Figure 8A
Figure 8D
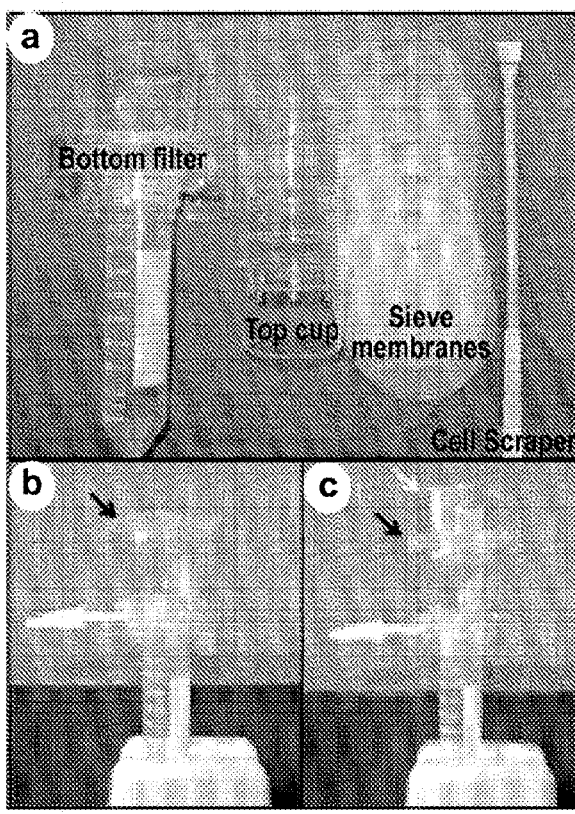
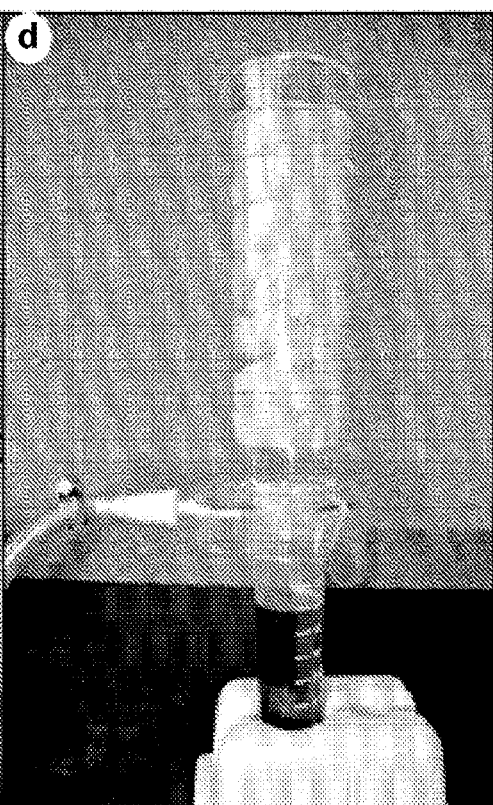
Figure 8B   Figure 8C

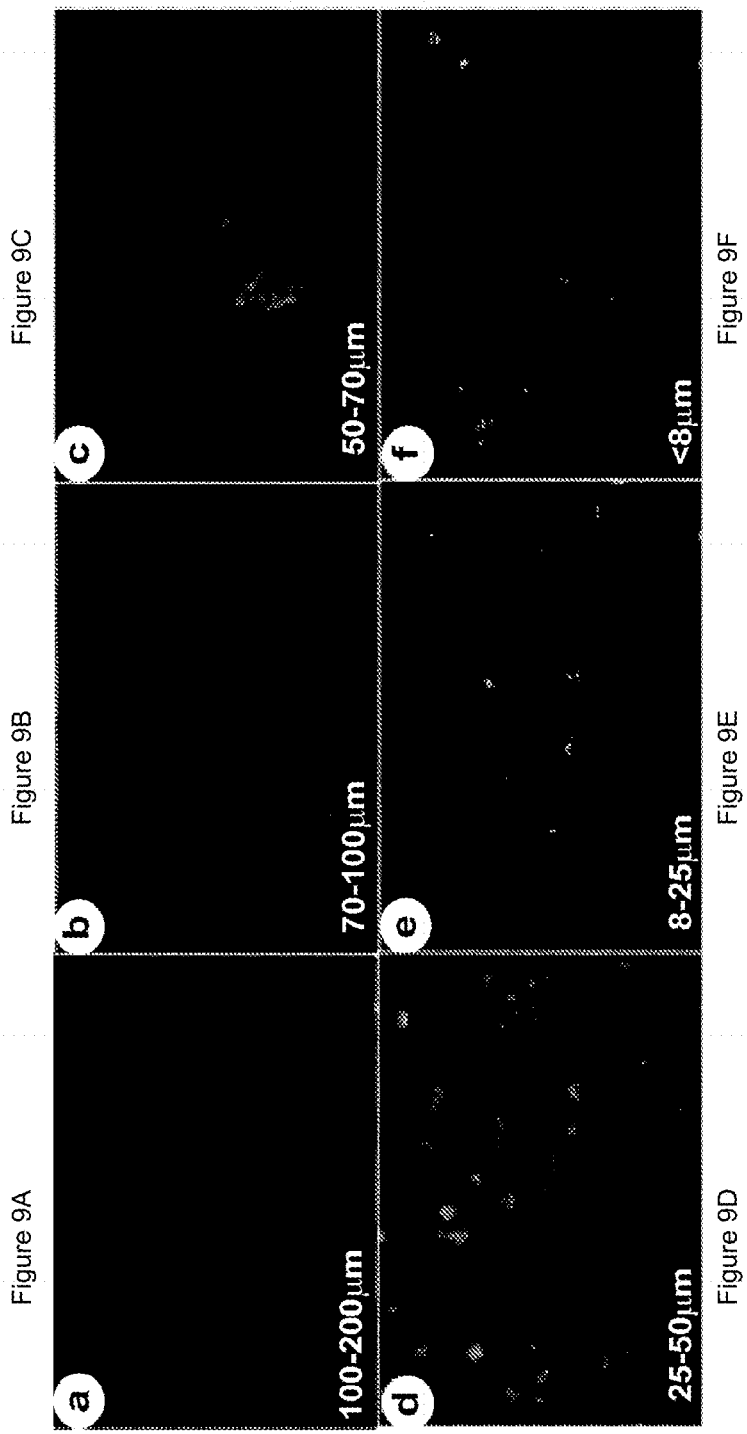

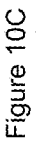
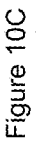
Figure 10A
Figure 10B
Figure 10C
Figure 10D

TISSUE ENGINEERED INTESTINE

This application is a continuation of U.S. Ser. No. 14/774,045, filed Sep. 9, 2015, which is a US National Phase application of PCT/US2014/028186, filed Mar. 14, 2014, claiming priority to U.S. Provisional Patent Application No. 61/783,655 filed Mar. 14, 2013, each of which are incorporated by reference herein in their entirety.

FIELD OF INVENTION

The invention provides for engineered intestinal construct and methods of making these constructs. The invention also provides for methods of treating short bowel syndrome or methods of repairing an intestine after resection comprising inserting an engineered intestinal construct into the intestine of a subject in need.

BACKGROUND

Heparin-binding epidermal growth factor (HB-EGF) was first identified in the conditioned medium of cultured human macrophages (Besner et al., Growth Factors, 7: 289-296 (1992), and later found to be a member of the epidermal growth factor (EGF) family of growth factors (Higashiyama et al., Science. 251:936-9, 1991). It is synthesized as a transmembrane, biologically active precursor protein (proHB-EGF) composed of 208 amino acids, which is enzymatically cleaved by matrix metalloproteinases (MMPs) to yield a 14-20 kDa soluble growth factor (sHB-EGF). Pro-HB-EGF can form complexes with other membrane proteins including CD9 and integrin $\alpha 3\beta 1$; these binding interactions function to enhance the biological activity of pro-HB-EGF. ProHB-EGF is a juxtacrine factor that can regulate the function of adjacent cells through its engagement of cell surface receptor molecules.

sHB-EGF is a potent mitogenic and chemoattractant protein for many types of cells. Similar to all members of the EGF family, HB-EGF binds to the "classic" or prototypic epidermal growth factor receptor (EGFR; ErbB-1). However, while the mitogenic function of sHB-EGF is mediated through activation of ErbB-1, its migration-inducing function involves the activation of ErbB-4 and the more recently described N-arginine dibasic convertase (NRDc, Nardilysin). This is in distinction to other EGF family members such as EGF itself, transforming growth factor (TGF)-$\alpha$ and amphiregulin (AR), which exert their signal-transducing effects via interaction with ErbB-1 only. In fact, the NRDc receptor is totally HB-EGF-specific. In addition, unlike most members of the EGF family, which are non-heparin binding, sHB-EGF is able to bind to cell-surface heparin-like molecules (heparan sulfate proteoglycans; HSPG), which act as low affinity, high capacity receptors for HB-EGF. The differing affinities of EGF family members for the different EGFR subtypes and for HSPG may confer different functional capabilities to these molecules in vivo. The combined interactions of HB-EGF with HSPG and ErbB-1/ErbB-4/NRDc may confer a functional advantage to this growth factor. Importantly, endogenous HB-EGF is protective in various pathologic conditions and plays a pivotal role in mediating the earliest cellular responses to proliferative stimuli and cellular injury.

Short bowel syndrome (SBS) is a consequence of massive small bowel resection performed in patients presenting with various diseases including inflammatory bowel disease, trauma, mesenteric vascular disease, volvulus, congenital atresias and neonatal necrotizing enterocolitis (NEC). Many thousands of patients with SBS each year depend on total parenteral nutrition (TPN) for survival, with the cost exceeding $50,000 per year per patient. Mortality remains high at 30% in the pediatric population. Approximately 50% of these deaths are attributable to hepatic failure from TPN-induced liver disease. In adults with SBS, 5% of deaths are related to complications of TPN. Surgical strategies in patients presenting with SBS include lengthening of the remnant small bowel, construction of intestinal valves to delay passage of intestinal material, and tapering procedures to improve peristalsis. However, such approaches are rarely feasible in adults owing to clinical complications including fistula formation and sepsis typically associated with Crohn's disease, the most prevalent underlying pathology within this patient subpopulation. In pediatric SBS patients treated with intestinal lengthening procedures, long-term survival is only 45%. Allogeneic transplantation of small bowel offers the potential for definitive functional rescue but may be associated with technical complications including high rates of graft rejection and complications associated with long-term immunosuppression. Clearly, there is a crucial clinical need for novel approaches to the treatment and management of SBS.

Tissue engineering and regenerative medicine technologies represent a next logical step towards the development of small intestinal substitutes. Such approaches require a cell source and biodegradable scaffold combined to produce a construct implanted into the body. The cell source and biodegradable scaffold must be capable of catalyzing the body's innate regenerative potential. The feasibility of a tissue engineered intestine begins with the remarkable regenerative ability of the intestinal epithelium. When a synthetic material is used to patch a full-thickness defect created in the small intestine of a rodent, enteric cells at the interface between the patch and the native mucosa migrate into the bare area and form organized epithelium. This observation led to efforts to implant enteric cells attached to polymer materials into the omentum of a rodent. The implantation of neonatal rodent intestinal OUs (partially digested pieces of the intestine) attached to biodegradable polymer scaffolds in the rodent omentum produces cystic structures lined by epithelial cells (Choi et al. Journal of pediatric surgery. 1998; 33:991-6). Patches of such tissue-engineered structures were successfully anastomosed to the native small intestine of rodents (Grikscheit et al. Annals of surgery. 2004; 240:748-54). After anastomosis, the rudimentary epithelium in the cystic structures developed into mature crypts and villi. When these tissue-engineered cysts were anastomosed to the side of the proximal small intestine in a rodent model of SBS, animals lost less weight and recovered sooner than the controls (Choi et al. Journal of pediatric surgery. 1998; 33:991-6).

Such tissue-engineered treatments would avoid problems associated with intestinal transplantation, including donor availability and complications of immunosuppressive therapy. Before such a strategy can be brought into clinical practice, however, considerable obstacles need to be overcome. The first obstacle is the source of cells to be used. In the last decade, studies have focused on using organoid units (OU) as the cell source for engineered intestine. OU are cell clusters that are isolated from full-thickness intestine, and represent a mixed population of differentiated and undifferentiated cells. This cell source is not efficient for tissue regeneration because differentiated epithelial cells no longer have the capacity to proliferate, and will likely undergo apoptosis. The second obstacle is the need to recreate peristaltic motion of the small intestine. Although tissues generated from intestinal organoids histologically resemble the mucosa, functional smooth muscle layers and neural plexuses are absent. The motility of enteric smooth muscle is primarily controlled by the myenteric plexuses, which comprise the enteric nervous system (ENS), and the ENS needs to be generated in tissue engineered intestine (TEI) to produce peristalsis.

SUMMARY OF INVENTION

The invention provides for an engineered intestine construct comprising a nanofiber scaffold seeded with neural stem cells (NSC), smooth muscle cells (SMC) and intestinal stem cells (ISC), wherein the nanofiber scaffold comprises HB-EGF polypeptide or a fragment thereof.

In addition, the invention provides for an engineered intestine construct comprising a nanofiber scaffold seeded with NSCs, SMCs and ISCs, wherein at least one of the neural stem cells, smooth muscle cells or intestinal stem cells overexpress HB-EGF polypeptide or a fragment thereof. The engineered intestine constructs of the invention may comprise a single layer nanofiber scaffold or a multilayer nanofiber scaffold.

In addition, the invention provides for the use of a custom designed cell filtration system to enrich intestinal stem cell-containing crypts to enhance mucosa engraftment for TEI; 2) incorporation of growth factors into scaffolds to improve the morphological and functional properties of TEI; 3) use of state-of-the-art technology to fabricate tissue engineering scaffolds that mimic the architecture and properties of native intestine and enhance the bio-environment for cell adhesion, proliferation, and differentiation.

The invention provides for engineered intestine construct comprising a multilayer nanofiber scaffold, wherein the multilayer nanofiber scaffold comprises at least an inner layer and an outer layer, wherein the outer layer comprises NSCs and SMCs, and wherein the inner layer comprises ISCs. The inclusion of multiple types of stem cells in the generation of the engineered intestine construct, e.g. NSCs and ISCs, allows for the generation of full thickness intestine with peristaltic and absorptive function. The ISC may be provided by seeding the scaffold with crypts and the inner layer of the scaffold may comprise crypts and ISCs.

The engineered intestine constructs of the invention may comprise a nanofiber scaffold wherein the scaffold comprises any biodegradable polymers. For example, may comprise nanofibers and/or macrofibers of one or more biodegradable polymer such as poly(glycolic acid)(PGA) nanofibers, Poly(ε-caprolactone) (PCL) nanofibers, Poly(-caprolactone-co-lactic acid) (PLC) nanofibers, Poly(L-lactic acid) (PLLA) nanofibers, Poly(D-lactic acid-co-glycolic acid) (PDLGA) nanofibers, Polydioxanone (PDO) nanofibers, Polyurethane (PU) nanofibers and PGA macrofibers or combinations thereof.

The multiple layers of the nanofiber scaffold allow for the use of polymers with varying pore size and strength through a single scaffold. For example, the presence of layer of different scaffold materials allow for multiple layers with a pore size gradient applied through the sidewall starting from the innermost layer with the biggest pores to the outermost layer with the smallest pores. This allows for the delivery of cells of different sizes to the scaffold and delivery of intact crypts to regenerate the mucosa layer.

The engineered intestine constructs of the invention may comprise a multilayer nanofiber scaffold comprising at least three layers, at least four layers, at least five layer, at least six layers, at least seven layers or at least eight layers. For example in one embodiment, the construct comprises an outer layer, at least one middle layer and an inner layer. In another embodiment, the engineered intestine construct comprises a multilayer nanofiber scaffold comprising an outer layer, a layer adjacent to the outer layer, a middle layer, a layer adjacent to the inner layer, such a layer of macrofibers, and an inner layer.

The multiple layers within the nanofiber scaffold of the invention may comprise the same or different biodegradable polymers and the layers include those comprising nanofibers and those comprising macrofibers.

In one embodiment, the engineered intestine construct comprises a nanofiber scaffold having an inner layer, at least one middle and the outer layer comprises of PDLGA. In a further embodiment, the engineered intestine construct comprises a scaffold having a layer of macrofibers, such as PGA macrofibers, between the inner layer and the middle layer, or adjacent to the inner layer. In another embodiment, the engineered intestine construct comprises a scaffold having a layer of PCL is in between the middle layer and the outer layer, or adjacent to the outer layer.

Any of the engineered intestine constructs of the invention may comprise a nanofiber scaffold wherein at least one of the layers comprises a HB-EGF polypeptide or an active fragment thereof. In some embodiments, the engineered intestine construct comprises a nanofiber scaffold wherein all the layers comprise HB-EGF polypeptide or an active fragment thereof. Alternatively, one or more the cell types seeded on the nanofiber scaffold may be transfected to express HB-EGF at a level above endogenous expression, including overexpression.

The HB-EGF polypeptide comprises the amino acid sequence of SEQ ID NO: 2 or is a fragment thereof that competes with HB-EGF for binding to the ErbB-1 receptor and has ErbB-1 agonist activity. A preferred HB-EGF fragments comprises amino acids of 74-148 of SEQ ID NO: 2 (human HB-EGF(74-148). Other fragments of HB-EGF which may be used to construct the engineered intestine constructs are fragments of SEQ ID NO: 2 which induce epithelial cell or somatic stem cell, such as NSC, MSC or ISC, proliferation, fragments of SEQ ID NO: 2 that induce epithelial cell or somatic stem cell, such as MSC or ISC, migration, fragments of SEQ ID NO: 2 that promote epithelial cell or somatic stem cell, such as MSC or ISC, viability, and a fragment of HB-EGF that protects epithelial cells or somatic stem cells, such as MSC or ISC form apoptosis or other types of cellular injury.

The HB-EGF polypeptide or fragments thereof include recombinant HB-EGF produced in *E. coli* and HB-EGF produced in yeast. The development of expression systems for the production of recombinant proteins is important for providing a source of protein for research and/or therapeutic use. Expression systems have been developed for both prokaryotic cells such as *E. coli*, and for eukaryotic cells such as yeast (*Saccharomyces, Pichia* and *Kluyveromyces* spp) and mammalian cells.

In one embodiment, the engineered intestine construct comprise an inner layer of nanofibers, e.g. of PLLA or PDLGA, that has a smooth lumen surface that prevent crypts from leaking out and comprises ISC, a layer of macrofibers, such as PGA, adjacent to the inner layer which serves to deliver cypts to regenerate the mucosa layer, a middle layer of nanofibers, such as PLLA or PDLGA, which serves to separate the crypts and SMCs, a layer of nanofibers, such as PCL, adjacent to the outer layer which serves to deliver SMCs and NSCs to regenerate the functional smooth muscle layer and an outer layer of nanofibers, such as PLLA or PDLGA, which serves to prevent SMCs from leaking out.

Exemplary multilayer scaffolds comprising either an inner and an outer layer or an inner, middle and outer layer are provided in Table 1. These exemplary scaffolds may comprise PGA as a nanofiber or macrofiber. In addition, these exemplary scaffolds may comprise one or more additional layers that are adjacent to the inner or outer layer. The invention is not limited to these exemplary scaffolds and the invention contemplates any combination of biodegradable polymers may be used to construct the scaffold.

TABLE 1

Exemplary Two Layer Scaffolds

| Outer Layer | Inner Layer |
|---|---|
| PGA | PGA |
| PCL | PCL |
| PLC | PLC |
| PLLA | PLLA |
| PDLGA | PDLGA |
| PU | PU |
| POD | PDO |
| PGA | PCL |
| PGA | PLC |
| PGA | PLLA |
| PGA | PDLGA |
| PGA | PU |
| PGA | PDO |
| PLC | PGA |
| PLC | PCL |
| PLC | PLLA |
| PLC | PDLGA |
| PLC | PU |
| PLC | PDO |
| PCL | PGA |
| PCL | PLC |
| PCL | PLLA |
| PCL | PDLGA |
| PCL | PU |
| PCL | POD |
| PLLA | PGA |
| PLLA | PLC |
| PLLA | PCL |
| PLLA | PDLGA |
| PLLA | PU |
| PLLA | PDO |
| PDLGA | PGA |
| PDLGA | PLC |
| PDLGA | PCL |
| PDLGA | PLLA |
| PDLGA | PU |
| PDGLA | PDO |
| PU | PGA |
| PU | PLC |
| PU | PCL |
| PU | PLLA |
| PU | PDLGA |
| PU | PDO |
| PDO | PGA |
| PDO | PCL |
| PDO | PLC |
| PDO | PLLA |
| PDO | PDLGA |
| PDO | PU |

Exemplary Three Layer Scaffolds

| Outer Layer | Middle Layer | Inner Layer |
|---|---|---|
| PGA | PGA | PGA |
| PGA | PGA | PCL |
| PGA | PGA | PLC |
| PGA | PGA | PLLA |
| PGA | PGA | PDLGA |
| PGA | PGA | PU |
| PGA | PGA | PDO |

TABLE 1-continued

| | | |
|---|---|---|
| PGA | PGA | PGA |
| PGA | PCL | PGA |
| PGA | PLC | PGA |
| PGA | PLLA | PGA |
| PGA | PDLGA | PGA |
| PGA | PU | PGA |
| PGA | PDO | PGA |
| PCL | PCL | PCL |
| PCL | PCL | PGA |
| PCL | PCL | PCL |
| PCL | PCL | PLLA |
| PCL | PCL | PDLGA |
| PCL | PCL | PU |
| PCL | PCL | PDO |
| PCL | PGA | PCL |
| PCL | PCL | PCL |
| PCL | PCL | PCL |
| PCL | PLLA | PCL |
| PCL | PDLGA | PCL |
| PCL | PU | PCL |
| PCL | PDO | PCL |
| PLC | PLC | PLC |
| PLC | PLC | PGA |
| PLC | PLC | PCL |
| PLC | PLC | PLLA |
| PLC | PLC | PDLGA |
| PLC | PLC | PU |
| PLC | PLC | PDO |
| PLC | PGA | PLC |
| PLC | PCL | PLC |
| PLC | PLLA | PLC |
| PLC | PDLGA | PLC |
| PLC | PU | PLC |
| PLC | PDO | PLC |
| PLLA | PLLA | PLLA |
| PLLA | PLLA | PGA |
| PLLA | PLLA | PCL |
| PLLA | PLLA | PLC |
| PLLA | PLLA | PDLGA |
| PLLA | PLLA | PU |
| PLLA | PLLA | PDO |
| PLLA | PGA | PLLA |
| PLLA | PCL | PLLA |
| PLLA | PLC | PLLA |
| PLLA | PDLGA | PLLA |
| PLLA | PU | PLLA |
| PLLA | PDO | PLLA |
| PDLGA | PDLGA | PDLGA |
| PDLGA | PDLGA | PGA |
| PDLGA | PDLGA | PCL |
| PDLGA | PDLGA | PLC |
| PDLGA | PDLGA | PLLA |
| PDLGA | PDLGA | PU |
| PDLGA | PDLGA | PDO |
| PDLGA | PGA | PDLGA |
| PDLGA | PCL | PDLGA |
| PDLGA | PLC | PDLGA |
| PDLGA | PLLA | PDLGA |
| PDLGA | PU | PDLGA |
| PDLGA | PDO | PDLGA |
| PU | PU | PU |
| PU | PU | PGA |
| PU | PU | PCL |
| PU | PU | PLC |
| PU | PU | PLLA |
| PU | PU | PDLGA |
| PU | PU | PDO |
| PU | PGA | PU |
| PU | PCL | PU |
| PU | PLC | PU |
| PU | PLLA | PU |
| PU | PDLGA | PU |
| PU | PDO | PU |
| PDO | PDO | PDO |
| PDO | PDO | PGA |
| PDO | PDO | PCL |
| PDO | PDO | PLC |
| PDO | PDO | PLLA |
| PDO | PDO | PDLGA |
| PDO | PDO | PU |
| PDO | PGA | PDO |

TABLE 1-continued

| | | |
|---|---|---|
| PDO | PCL | PDO |
| PDO | PLC | PDO |
| PDO | PLLA | PDO |
| PDO | PDLGA | PDO |
| PDO | PU | PDO |

In another aspect, the invention provides for methods of generating an engineered intestine construct comprising a) preparing a nanofiber scaffold by electrospinning a polymer to a target fiber diameter and porosity, b) embedding an HB-EGF polypeptide or fragment thereof on at least one layer of the scaffold, c) seeding the scaffold with intestinal stem cells, neural stem cells and smooth muscles cells, and d) culturing the cells in the scaffold to form a construct that will form a mature intestine upon insertion into a subject. A number of endpoints could be used to determine when an engineered intestine construct of the invention is in condition for insertion into a subject in need, such as the number of cells engrafted on the scaffold, a decrease in cell apoptosis within the construct, formation of mature intestine within the construct. Mature intestine is refers to intestine that contains mucosa, smooth muscle layers and an enteric nervous system.

"Target fiber diameter and porosity" refers to fibers that exhibit one or more of the following qualities: matches mechanical requirements of the engineered organ, allow for uniform cell seeding, promotes cell attachment, communication and signaling, prevents cells from penetrating the scaffold and mimics the native organ.

The invention provides for methods of generating an engineered intestine construct wherein the culturing step is carried out in a bioreactor such as a perfusion system bioreactor. In addition, the invention provides for method of generating an engineered intestine construct wherein the nanofiber scaffold comprises at least an outer and an inner layer, and these constructs may further comprise a middle layer.

In any of the method of the invention, the intestinal stem cells are seeded on the inner layer and may be provided by seeding crypts on the inner layer. Furthermore, in any of the methods of the invention, the neural stem cells and smooth muscle cells are seeded on the outer layer.

The methods of the invention may generate engineered intestine constructs that comprise multiple layers within the nanofiber scaffold, and these layers may comprise the same or different biodegradable polymers and the layers include those comprising nanofibers and those comprising macrofibers. The layers of the scaffold may comprise nanofibers and/or macrofibers of a biodegradable polymer such as poly(glycolic acid)(PGA) nanofibers, Poly(ε-caprolactone) (PCL) nanofibers, Poly(-caprolactone-co-lactic acid) (PLC) nanofibers, Poly(L-lactic acid) (PLLA), Poly(D-lactic acid-co-glycolic acid) (PDLGA), Polyurethane (PU) nanofibers, Polydioxanone (PDO) nanofibers and PGA macrofibers or combinations thereof. In particular, the nanofibers may comprise PDLGA or PLLA.

In another aspect, the invention provides for methods of method of treating short bowel syndrome in a subject comprising attaching an engineered intestine construct of the invention under conditions where the construct will implant within the intestine of the subject.

The invention also provides for use of the engineered intestine construct of the invention for the preparation of a medicament for treating short bowel syndrome wherein the medicament is administered to subject under conditions wherein the intestine implants within the subject. The invention also provides for engineered intestine constructs of the invention for use in treating short bowl syndrome wherein the engineered intestine construct implants within the intestine of the subject.

The invention also provides for methods of repairing the intestine of a subject undergoing intestinal resection comprising attaching the engineered intestine construct of the invention under conditions wherein the construct will implant within the intestine of the subject. The term "intestinal resection" includes small bowel resection, large bowel resection and colectomy.

The invention also provides for use of the engineered intestine construct of the invention for the preparation of a medicament for repairing the intestine of subject undergoing intestinal resection wherein the medicament is administered under conditions wherein the engineered intestine construct of the invention attaches to and implants within the intestine of the subject. The invention also provides for an engineered intestine construct of the invention for use in repairing the intestine of a subject undergoing intestinal resection wherein the engineered intestine construct of the invention attaches to and implants within the intestine of the subject.

Furthermore, the invention provides for methods of treating short bowel syndrome in a subject or repairing the intestine of a subject suffering from inflammatory bowel disease, trauma, mesenteric vascular disease, vovlulus, congenital atresias, neonatal necrotizing enterocolitis, Crohn's disease, ischemia, intestinal blockage, bowel obstruction, regional ileitis, regional enteritis, colorectal cancer such as colorectal cancer and other tumors that invade the intestine, carcinoid tumor, Merkel's diverticulum, precancerous polyps, diverticulitis, intestinal bleeding, intussusceptions, or ulcerative colitis.

The invention also provides for use of the engineered intestine construct of the invention for the preparation of a medicament for treating short bowel syndrome in a subject or for repairing the intestine of a subject wherein the subject is suffering from inflammatory bowel disease, trauma, mesenteric vascular disease, vovlulus, congenital atresias, neonatal necrotizing enterocolitis, Crohn's disease, ischemia, intestinal blockage, bowel obstruction, regional ileitis, regional enteritis, colorectal cancer such as colorectal cancer and other tumors that invade the intestine, carcinoid tumor, Merkel's diverticulum, precancerous polyps, diverticulitis, intestinal bleeding, intussusceptions, or ulcerative colitis.

The invention also provides for engineered intestine constructs for use in treating short bowel syndrome in a subject or repairing the intestine of a subject, wherein the subject is suffering from inflammatory bowel disease, trauma, mesenteric vascular disease, vovlulus, congenital atresias, neonatal necrotizing enterocolitis, Crohn's disease, ischemia, intestinal blockage, bowel obstruction, regional ileitis, regional enteritis, colorectal cancer such as colorectal cancer and other tumors that invade the intestine, carcinoid tumor, Merkel's diverticulum, precancerous polyps, diverticulitis, intestinal bleeding, intussusceptions, or ulcerative colitis.

In another aspect, the invention provides for methods of enriching a cell sample for a particular cell type comprising contacting a cell sample with multiple sieve membranes wherein the membranes are aligned in descending order according to pore size, wherein the cell sample contacts the membrane with the largest pore size first and wherein the cell sample comprises multiple cell types, filtering the cell sample through the membranes and recovering the enriched cell sample. In particular, the methods of the invention are used to enrich intestinal cells in crypts for use in generating the TEI of the invention. The cell sample comprising multiple cell types includes samples comprising at least two different cell types or a sample comprising differentiated and undifferentiated cells or cells at different states of differentiation.

An enriched cell sample may comprise one cell type or two cells types or three cells type or more. The term "enriched" refers to improving the quality of the cell sample by removing unneeded cell types or reducing the number of cell types within a sample. An exemplary enriched sample comprises intestinal stem cells and their neighboring cells including paneth cells within crypts. Another example of an enriched cell sample consists of differentiated cell-containing villi, which are separated from the stem cell-containing crypts by their larger size.

The invention provides for engineered tissue construct comprising a nanofiber construct seeded with NSCs, SMCs and ISCs. An innovation of the invention is the use of multiple stem cell types in order to generate full thickness intestine with peristaltic and absorptive function. Another innovation of the invention is the use of state-of-the-art technology to fabricate tissue engineering scaffolds that mimic the architecture and properties of native intestine and enhance the bio-environment for cell adhesion, proliferation, and differentiation. The present invention combines cell therapy with novel nanofiber technology to regenerate full-thickness, functional intestine.

The engineered intestine constructs of the invention avoid problems associated with intestinal transplantation, including donor availability and complications of immunosuppressive therapy. In addition, the engineered tissue constructs avoid the use of organoid units (OU), or cell clusters that comprise a mixed population of differentiated and undifferentiated cells, and the presence of differentiated epithelial cells do not have the capacity to proliferate which does not promote tissue regeneration.

The present invention utilizes intestinal crypts enriched in ISC delivers concentrated ISC in order to enhance mucosa formation. Intestinal crypts are a gland located in the epithelial ling of the small intestine and the colon. The crypts comprise an epithelium that comprises goblet cell and enterocytes. New epithelium is formed within the crypts and therefore the basal portion of the crypt comprises multipotent stem cells, e.g. ISCs.

The second obstacle is the need to recreate peristaltic motion of the small intestine. Although tissues generated from intestinal organoids histologically resemble the mucosa, functional smooth muscle layers and neural plexuses are absent. The motility of enteric smooth muscle is primarily controlled by the myenteric plexuses, which comprise the enteric nervous system (ENS). The ENS needs to be generated in tissue engineered intestine (TEI) to produce peristalsis. The present invention overcomes this obstacle by using specially designed electrospun nanofiber scaffolds modeled after native intestinal architecture with circumferentially and longitudinally aligned nanofibers in the middle and outside layer of the scaffold, respectively, for delivering a mixture of smooth muscle cells (SMCs) and NSCs. The seeded SMC migrate and proliferate along the nanofibers and will eventually be encapsulated by extracellular matrix (ECM) to form muscularis interna and externa. The implanted NSC in the newly regenerated intestine will differentiate to form myenteric plexuses which will communicate with the native ENS to perform peristalsis.

Nanofiber Scaffolds

The engineered intestine constructs of the invention comprise a nanofiber scaffold. The nanofiber scaffolds used in the invention are specially designed electrospun nanofiber scaffolds seeded with a mixture of smooth muscle cells (SMCs) and neural stem cells (NSCs), which is one of the innovations and goals of this proposal. The nanofiber scaffolds may comprise one layer or multiple layers of nanofibers or macrofibers of biodegradable polymers.

Electrospinning has been used to fabricate tissue engineered scaffolds comprising non-woven, three-dimensional, porous, nanoscale fiber-based matrices. The characteristics of fibrous scaffolds, such as high surface area to volume ratio with similar structural morphology to the fibrillar extracellular matrix (ECM) found in vivo, suggest that they may serve as effective tissue engineering scaffolds. Moreover, the alignment of nanofibers and the porosity of the scaffold can be tailored to match the mechanical requirements of the target organ.

Electrospinning of nanofibers for tissue engineering has a number of benefits (Lannutti et al. Mat. Sci. Engin: C 27: 504-509, 2007). These include cost-effectiveness and that the scaffolds can be created in a nanoscaled form resembling the extracellular matrix allowing for more natural cellular proliferation. Electrospinning also allows for the adjustment of fiber diameter and alignment to guide cellular infiltration. Pore sizes can also be adjusted and the scaffolds tend to have large surface areas with open, connected porous arrangements of 70-90% relative porosity. This allows for both enhanced drug delivery and room for cell adhesion and proliferation. Finally, multiple different polymers and blends of polymers can be used to create the ideal mechanical and degradative features for tissue engineering. These alterations in scaffold structure allow for improved cell-scaffold interactions and may promote cell migration and proliferation to optimize the tissue engineered structure or organ. Electrospinning of nanofiber scaffolds also allows for polymers to be blended or layered to produce a more biomimetic scaffold than is possible using a single material. Ultimately, a blend or layering of these polymers may produce the most ideal scaffold composition in this application. The nanofiber scaffold may comprise a biodegradable polymers including poly(glycolic acid) (PGA), polyesters such as poly(ε-caprolactone) (PCL) and poly (ε-caprolactone-co-lactic polylactic acid (PCL), and polylactic acid copolymers such as poly(L-lactic acid (PLLA) and poly (D-lactic acid-co-glycolic acid (PDLGA), polyurethane (PU), polyanhydrides; Polydioxanone (PDO) nanofibers; poly alkyl cyanoacrylates such as n-butyl cyanoacrylate and isopropyl cyanoacrylate; polyacrylamides; poly(orthoesters); polyphosphazenes; polypeptides; polyurethanes; and combinations of such polymers.

While the multilayer nanofiber scaffolds of the invention are primarily composed of nanofibers, the invention provides for scaffolds that include layers of macrofibers such as PGA.

In one aspect, the nanofiber scaffold comprises the copolymer of glycolic acid and lactic acid (PLGA), such as Poly(D-lactic acid-co-glycolic acid) (PDLGA) having a proportion between the lactic acid/glycolic acid units ranging from about 100/0 to about 25/75. The average molecular weight ("MW") of the polymer will typically range from about 6,000 to 700,000 and preferably from about 30,000 to 120,000, as determined by gel-permeation chromatography using commercially available polystyrene of standard molecular weight, and have an intrinsic viscosity ranging from 0.5 to 10.5.

Poly(ε-caprolactone) (PCL) is a semicrystalline material with good mechanical properties. PCL is one of the most widely used biodegradable polyesters for medical applications because of its biocompatibility, biodegradability, and flexibility. Scaffolds fabricated using PCL are more resistant to hydrolysis, and consequently they are capable of supporting the viability, proliferation, and differentiation status of implanted cells. Poly(c-caprolactone-co-lactic acid) (PLC), a poly(lactic acid) (PLA) and PCL copolymer, has a similar Young's modulus (the ratio of the uniaxial stress over the uniaxial strain in the range of stress in which Hooke's Law holds), to PCL and native intestine as demonstrated in our preliminary data, but possesses better mechanical strength in vitro, allowing the tubular structure to be maintained in a hydrated state. This is especially beneficial for maintaining continuity of the lumen with native intestine. In this proposal, PCL and PLC will be used to fabricate tri-layer scaffolds with a pore size gradient applied through the sidewall starting from the innermost layer with the biggest pores to the outermost layer with the smallest pores. A non-woven innermost layer with the biggest pore size will allow for the accommodation of crypts and the regeneration of mucosa. Circumferentially and longitudinally aligned nanofibers in the middle and outermost layers, respectively, are intended for the residence of SMCs and NSCs and eventually the formation of muscularis interna and externa. Others have demonstrated increased SMC attachment and proliferation on aligned nanofibers compared to randomly oriented nanofiber matrices (Levin et al. Expert review of medical devices. 2011; 8:673-5). This can be explained by the "contact guidance" theory, which illustrates that a cell has the maximum probability of migrating in directions that are associated with chemical, structural, and/or mechanical properties of the substratum. Aligned nanofibers represent an effective approach to control cell orientation and migration in tissue engineering.

In the present invention, different scaffold materials were used to fabricate multi-layered scaffolds with a pore size gradient applied through the sidewall starting from the innermost layer with the biggest pores to the outermost layer with the smallest pores. A non-woven innermost layer with the biggest pore size will allow for the accommodation of SC-containing crypts and the regeneration of mucosa. Circumferentially and longitudinally aligned nanofibers in the middle and outermost layers, respectively, are intended for the residence of SMC and NSC and eventually the formation of muscularis interna and externa. Others have demonstrated increased SMC attachment and proliferation on aligned nanofibers compared to randomly oriented nanofiber matrices. This can be explained by the "contact guidance" theory, which illustrates that a cell has the maximum probability of migrating in directions that are associated with chemical, structural, and/or mechanical properties of the substratum. Aligned nanofibers represent an effective approach to control cell orientation and migration in tissue engineering. The use of multi-layered nanofiber scaffolds, with seeding of the inner layer with SC-containing crypts, and seeding of the outer layer with SMC and NSC, represents a completely novel methodology that has never been previously described.

In order to accelerate and mature tissue formation in vitro and in vivo, heparin binding EGF-like growth factor (HB-EGF) will be embedded into the tri-layer scaffold. Multiple experiments have shown that administration of HB-EGF protects the intestines from experimental NEC, intestinal ischemia/reperfusion injury, and hemorrhagic shock and resuscitation. HB-EGF protects the intestines from experimental NEC and other forms of intestinal injury by protecting ISC from injury, by promoting the proliferation and migration of enterocytes, by increasing microvascular villous blood flow, by increasing gut barrier function, and by reducing intestinal apoptosis. It also known that HB-EGF promotes the migration and proliferation of mesenchymal stem cells (MSC), and protects MSC from anoxia/reoxygenation-induced apoptosis in vitro. To generate the engineered intestine constructs, HB-EGF was embedded into the nanofibers using $CO_2$-assisted infusion of HB-EGF into electrospun tri-layer nanofiber scaffolds will mimic the native structural and chemical environment of the intestine, improve tissue regeneration, and provide a significant advancement in the production of tissue engineered intestine. Lastly, to facilitate cell adhesion and inclusion, the temperature-sensitive hydrogel pluronic F-127 will be mixed with cells prior to seeding of nanofiber scaffolds. Others have shown that ~30-40% of seeded cells pass through or are released from open spaces on the surface of polymer scaffolds upon cell seeding (Yu et al. J Surg Res. 2012; 172:165-76). Pluronic F-127 is a triblock copolymer composed of a central hydrophobic chain of poly(propylene oxide) flanked by two hydrophilic chains of poly(ethylene oxide). It exhibits low viscosity below room temperature and changes to a viscous soft gel at body temperature (~37° C.). The combination of nanofiber scaffolds and hydrogel will prevent cells from detaching. It is expected that the tissue engineered intestine constructs of the invention have similar intestinal morphology and function when compared to with native intestine Fabrication of Nanofiber Scaffolds The nanofiber scaffolds of the invention can be fabricated using any method known in the art. In one embodiment, the multilayer nanofiber scaffolds are fabricated using electrospinning. This fabrication method allows the generation of nanofibers with a pore size gradient that allows for seeding of different sized cells. In particular, nanofibers with greater pore size assists seeding the scaffold with cypts.

Electrospinning Multi-Layer Fiber Scaffolds

Electrospinning is driven by the application of a high voltage, typically between 0 and 30 kV, to a droplet of a polymer solution or melt. The liquid polymer is typically ejected from a capillary at a flow rate between 0 and 50 ml/h to create a condition of charge separation between two electrodes and within the polymer solution to produce a jet of polymer. A typical polymer solution would consist of a polymer such as polycaprolactone, polystyrene, or polyethersulfone and a solvent such as 1,1,1,3,3,3-Hexafluoro-2-propanol, N,N-Dimethylformamide, Acetone, or Tetrahydrofuran in a concentration range of 5-50 wt %. As the jet of polymer solution travels toward the electrode it is elongated into sub-micron diameter fibers typically in the range of 0.1-50 µm.

Dual Layer Electrospinning

During electrospinning polymer fibers are driven toward a collector by charge separation caused by applied voltage. The collector is typically a conductive surface such as aluminum or copper, but can also be covered by a thin layer of plastic between 0.001-0.1 inches thick. The charge that drives electrospinning toward the collector comes from mobile ions within the polymer solution or melt [ ]. The jet of polymer that is produced will have a net positive or negative charge depending upon the polarity of the DC voltage applied to the electrode(s). When the jet solidifies on the collector surface the charge will build up as subsequent fiber layers are collected. It is believed that as the charge builds up on the surface fiber with similar charge will be repelled leading to a lower density and lower uniformity of fiber collected. A means of collecting a large uniform layer of fiber onto a collector is to electrospin for a period of time using one voltage polarity i.e. negative followed by electrospinning with the opposite polarity i.e. positive for a period of time. Since opposite charges attract an increased thickness of fiber may be deposited or two different materials/fiber diameters can be used in one scaffold.

Stem Cell Environment

In cell culture it is desirable to have a three dimensional surface on which the cells will differentiate and expand. In stem cell culture a three dimensional surface may help the cells maintain their "stemness" as opposed to differentiating down an undesired pathway. When cultured on a two dimensional surface i.e. flat polystyrene the cells often differentiate into adipocytes or other undesired cell phenotypes. Ideally, the three dimensional scaffold would have a porosity greater than 10 μm to allow cell penetration, but could have layers with pore sizes smaller than 10 μm to prevent cells from penetrating through the scaffold. Using multi-layer electrospinning a dense layer of small diameter fiber with average pore diameter less than 10 μm is deposited followed by the deposition of large porosity fibers with an average pore diameter greater than 10 μm. This configuration will allow the cells to penetrate the large porosity fiber to the small pore size fiber.

Material Selection

Choosing a material that can accurately mimic the mechanical properties of the native organ/tissue is critical to promote proper stem cell differentiation and facilitating normal tissue function. Materials may be non-resorbable for permanent implantation or may be designed to slowly degrade while the host body rebuilds the native tissue until the implanted prosthesis is completely resorbed. Permanent polymers may include polyurethane, polycarbonate, polyester terephthalate and degradable materials may include polycaprolactone, polylactic acid, polyglycolic acid, gelatin, collagen, or fibronectin. The fibers may be electrospun onto a form with the desired prosthesis shape.

Fiber Orientation and Composite Structure

Closely mimicking the structure of the native organ is necessary to replicate the organ function. By controlling the orientation of the fibers and assembling a composite structure of different materials and/or different fiber orientations it is possible to control and direct cell orientation and differentiation.

Scaffold Porosity

The scaffold needs to allow complete cellular penetration and uniform seeding for proper function and prevention of necrotic areas developing. If the fiber packing is too dense, then cells will not be able to penetrate or migrate from the exposed surfaces into the inner portions of the scaffold. However, if the fiber packing is not close enough, then the attached cells will not be able to properly fill the voids, communicate and signal each other and a complete tissue or organ will not be developed. Controlling the fiber diameter is one way to change the scaffold porosity as the porosity scales with fiber diameter. Alternatively, blends of different polymers may be electrospun together and one polymer preferentially dissolved to increase scaffold porosity.

Fiber orientation can be altered in each layer of a composite or sandwich scaffold in addition to the material and porosity to most closely mimic the native tissue.

Tissue Culture Vessels

Those of ordinary skill in the art will readily appreciate that the cell culture and bioengineering methodologies described herein may be carried out in on a variety of environments or substrates (i.e., vessels or containers). SMCs, NSCs and ISCs are anchorage dependent, and therefore to grow in culture these cells require a nontoxic, biologically inert, and optically transparent surface that will allow cells to attach and allow movement for growth. Tissue culture vessels or plates include specially-treated polystyrene plastic that are supplied sterile and are disposable. These include Petri dishes, multi-well plates, microtiter plates, roller bottles, screwcap flasks (T-25, T-75, T-150 cm2 of surface area), culture bags or any container capable of holding cells, preferably in a sterile environment.

In one embodiment of the present invention, a bioreactor is also useful for bioengineering the engineered intestine constructs. In particular, the invention contemplates generation of the engineered intestine constructs using a perfusion provides bioreactor. For example, several manufacturers currently make devices that can be used to grow cells and be used in combination with the methods of the present invention. See for example, Celdyne Corp., Houston, Tex.; Unisyn Technologies, Hopkinton, Mass.; Synthecon, Inc. Houston, Tex.; Aastrom Biosciences, Inc. Ann Arbor, Mich.; Wave Biotech LLC, Bedminster, N.J. Further, patents covering such bioreactors include U.S. Pat. Nos. 6,096,532; 6,001,642, 5,985,653; 5,888,807; 5,688,687, 5,605,835, 5,190,878, which are incorporated herein by reference.

There are a number of different kinds of bioreactors, devices designed to provide a low-shear, high nutrient perfusion environment, available on the market. For example, the invention may be carried out in a rotating wall bioreactor, which consists of a small inner cylinder, the substrate for the electrospinning process, positioned inside a larger outer cylinder. Although the electrospun matrix can be fabricated on the inner cylinder, other locations within the bioreactor also may be used for placement of the matrix for seeding. The gap between the inner and outer cylinders serves as the culture vessel space for cells. Culture medium is oxygenated via an external hydrophobic membrane. The low shear environment of the rotating bioreactor promotes cell-cell and cell-extracellular matrix (ECM) interactions without the damage or "washing away" of nutrients that occurs with active stirring.

The cells that are seeded on the nanofiber scaffold may be grown in a hydrogel or another extracellular matrix. Hyrdogels may are formed from synthetic (e.g., poly(ethylene glycol), poly (hydroxyethyl methacrylate)) and naturally occurring polymers (e.g., collagen, hyaluronan, heparin), and are useful 3D models of tissue culture due to their high water content and ability to form in the presence of cells, proteins and DNA.

Fibrin gel is a suitable material that may be used for organ replacement. Fibrin gel is a network made up of monomeric fibrin molecules generated by activation of fibrinogen by thrombin. This biopolymer is known to be involved in hemostatis and wound healing. Fibrin is a biodegradable material that has been used for temporary tissue replacement and as an absorbable implant material.

Another particular example of a suitable material is fibrous collagen, which may be lyophilized following extraction and partial purification from tissue and then sterilized. Matrices may also be prepared from tendon or dermal collagen as may be obtained from a variety of commercial sources, such as, e.g., Sigma and Collagen Corporation.

In addition, lattices made of collagen and glycosaminoglycan (GAG) such as that described in Yannas & Burke, U.S. Pat. No. 4,505,266, may be used in the practice of the invention. The collagen/GAG matrix may effectively serve as a support or "scaffolding" structure into which repair cells may migrate.

The various collagenous materials may also be in the form of mineralized collagen. For example, the fibrous collagen implant material termed UltraFiber™, as may be obtained from Norian Corp., (1025 Terra Bella Ave., Mountain View, Calif., 94043) may be used for formation of matrices. U.S. Pat. No. 5,231,169, incorporated herein by reference, describes the preparation of mineralized collagen through the formation of calcium phosphate mineral under mild agitation in situ in the presence of dispersed collagen fibrils.

At least 20 different forms of collagen have been identified and each of these collagens may be used in the practice of the invention. For example, collagen may be purified from hyaline cartilage, as isolated from diarthrodial joints or growth plates. Type II collagen purified from hyaline cartilage is commercially available and may be purchased from, e.g., Sigma Chemical Company, St. Louis. Type I collagen from rat tail tendon may be purchased from, e.g., Collagen Corporation. Any form of recombinant collagen may also be employed, as may be obtained from a collagen-expressing recombinant host cell, including bacterial yeast, mammalian, and insect cells. When using collagen as a matrix material it may be advantageous to remove what is referred to as the "telopeptide" which is located at the end of the collagen molecule and known to induce an inflammatory response.

Somatic Stem Cells

Stem cells are cells with the ability to divide for indefinite periods in culture to give rise to specialized cells. The term "somatic stem cell" or "adult stem cell" refers to undifferentiated cells, found among differentiated cells within a tissue or organ, which has the capacity for self-renewal and differentiation. The somatic stem cells can differentiate to yield some or all of the major specialized cell types of the renewable tissue or organ. The primary role of somatic stem cells is to maintain and repair the tissue in which they are found.

Somatic stem cells may be used for transplantation. For example, the invention provides for methods of transplanting somatic stem cells to treat intestinal injury or to reduce the damage to the intestine in a patient suffering from an intestinal injury. Exemplary somatic stem cells include hematopoietic stem cells, mesenchymal stem cells, intestinal stem cells, skeletal stem cells, hepatocyte stem cells, neural stem cells, skin stem cells, endothelial stem cells, mammary stem cells, intestinal stem cells and neural crest stem cells.

The stem cells seeded on the scaffolds of the invention may be isolated from a subject to generate the engineered intestine construct. In addition, established cell lines may be used to seed to the scaffolds of the invention to generate the engineered intestine construct. Alternatively, intestine tissue is minced and organoids are grown and these cells are used to seed the scaffolds for generation of the intestine scaffold construct.

Mesenchymal Stem Cells

"Mesenchymal stem cells" (MSC) are non-hematopoietic, pluripotent, self-renewing progenitor cells with a characteristic spindle-shaped morphology. These cells are derived from immature embryonic connective tissue (mesoderm layer).

Mesenchymal stem cells (MSC) have the ability to differentiate into different cell lineages and can stimulate wound healing via paracrine signaling pathways. Preclinical studies have shown that MSC can regulate the host immune response, thus avoiding recognition and subsequent rejection by recipients. The robust, self-renewing, multilineage differentiation potential of MSC makes these cells very desirable candidates for possible clinical cellular therapy. Baksh et al., J Cell Mol Med 2004; 8(3):301-16. Ongoing investigations are exploring ways to optimize MSC efficacy prior to therapeutic delivery, including preconditioning by exposure to hypoxia, Hu et al., J Thorac Cardiovasc Surg 2008; 135(4):799-808, growth factors, Hahn et al., J Am Coll Cardiol 2008; 51(9):933-43, and various cytokines. Gui et al., Mol Cell Biochem 2007; 305(1-2):171-8, Pasha et al., Cardiovasc Res 2008; 77(1):134-42, Liu et al., Acta Pharmacol Sin 2008; 29(7):815-22.

MSC have been shown to contribute to the maintenance and regeneration of various connective tissues. (Pittenger et al., Science 1999; 284(5411):143-7) MSC differentiate into a number of cell types, including chondrocytes, bone, fat, cells that support the formation of blood, and fibrous connective tissue.

MSC are mobilized from bone marrow in response to tissue injury to aid in repair after a variety of end organ injury-models including models of myocardial infarction (Kawada et al., Blood 2004; 104:3581-7), spinal cord injury (Koda et al., Neuroreport 2005; 16:1763-7), renal ischemia/reperfusion injury (Togel et al., Am J Physiol Renal Physiol 2005; 289:F31-42) and intestinal radiation injury (Zhang et al., J Biomed Sci 2008; 15:585-94).

Mesenchymal stem cells may be isolated from various tissues including but not limited to bone marrow, peripheral blood, blood, placenta, and adipose tissue and amniotic fluid (denoted as AF-MCS herein) Exemplary methods of isolating mesenchymal stem cells from bone marrow are described in (Phinney et al., J Cell Biochem 1999; 72(4): 570-85), from amniotic fluid (Baghaban et al., Arch Iran Med 2011; 14(2):96-103), from peripheral blood are described by Kassis et al. (Bone Marrow Transplant. 2006 May; 37(10):967-76), from placental tissue are described by Zhang et al. (Chinese Medical Journal, 2004, 117 (6):882-887), from adipose tissue, placental and cord blood mesenchymal stem cells are described by Kern et al. (Stem Cells, 2006; 24:1294-1301).

The mesenchymal stem cells may be characterized using structural phenotypes. For example, the cells of the present invention may show morphology similar to that of mesenchymal stem cells (a spindle-like morphology). Alternatively or additionally, the MSC may be characterized by the expression of one or more surface markers. Exemplary MSC surface markers include but are not limited to CD105+, CD29+, CD44+, CD90+, CD73+, CD105+, CD166+, CD49+, SH(1), SH(2), SH(3), SH(4), CD14−, CD34−, CD45−, CD19−, CD5−, CD20−, CD11B−, FMC7− and HLA class 1 negative. Other mesenchymal stem cell markers include but are not limited to tyrosine hydroxylase, nestin and H-NF.

Examples of cells derived from mesenchymal cells include (1) cells of the cardiovascular system such as endothelial cells or cardiac muscle cells or the precursor cells of the cells of the cardiovascular system, and cells having the properties of these cells; (2) cells of any one of bone, cartilage, tendon and skeletal muscle, the precursor cells of the cells of any one of bone, cartilage, tendon, skeletal muscle and adipose tissue, and the cells having the properties of these cells; (3) neural cells or the precursor cells of neural cells, and the cells having the properties of these cells; (4) endocrine cells or the precursor cells of endocrine cells, and the cells having the properties of these cells; (5) hematopoietic cells or the precursor cells of hematopoietic cells, and the cells having the properties of these cells; and (6) hepatocytes or the precursor cells of hepatocytes, and the cells having the properties of these cells.

Methods of mesenchymal cell culture are well known in the art of cell culturing (see, for example, Friedenstein et al., Exp Hematol 1976 4, 267-74; Dexter et al. J Cell Physiol 1977, 91:335-44; and Greenberger, Nature 1978 275, 7524). For example, mesenchymal cells are derived from a source selected from the group consisting of endothelial cells, cardiac muscle cells, bone cells, cartilage cells, tendon cells, skeletal muscle cells, bone cells, cartilage cells, tendon cells, adipose tissue cells, neural cells, endocrine cells, hematopoietic cells, hematopoietic precursor cells, bone marrow cells, and the precursor cells thereof, hepatocytes, and hepatocyte precursor cells.

The marrow or isolated mesenchymal stem cells can be autologous, allogeneic or from xenogeneic sources, and can be embryonic or from post-natal sources. Bone marrow cells may be obtained from iliac crest, femora, tibiae, spine, rib or other medullary spaces. Other sources of human mesenchymal stem cells include embryonic yolk sac, placenta, umbilical cord, periosteum, fetal and adolescent skin, and peripheral, circulating blood.

Intestinal Stem Cells

The lining of the intestines is composed of millions of villi and crypts, which form a barrier against bacterial invasion. The intestinal epithelium is the most rapidly proliferating tissue in adult mammals. Intestinal stem cells (ISCs) are responsible for self-renewal of the epithelium, and also represent a reserve pool of cells that can be activated after injury. The estimated number of stem cells is 4-6 per crypt. (Barker et al., Gastroenterology 2007; 133:1755-1760) Stem cells have been proven to be crucial for the recovery and regeneration of several tissues including the intestinal epithelium. (Vaananen et al., Ann Med 2005; 37:469-479). In the past, ISCs were identified at position +4 from the crypt bottom, directly above the Paneth cells. It is now thought that there may be two populations of ISCs, a slowly cycling quiescent reserve population above the Paneth cells (upper stem cell zone, USZ) (the +4 cells), and a more rapidly cycling (every 24 hours) active pool of crypt base columnar (CBC) cells located between the Paneth cells (lower stem cell zone, LSZ). The more active ISCs may maintain homeostatic regenerative capacity of the intestine with the more quiescent ISCs held in reserve. (Scoville et al., Gastroenterology 2008 136: 849-864) Several signaling pathways including the Wnt/b-catenin, BMP, RTK/PI3K and Notch cascades are critical to ISC self-renewal and proliferation. Among them, Wnt/b-catenin is the signature/signaling pathway, and its downstream regulated genes represent potential ISC markers. The Wnt/b-catenin target gene LGR5 has been recently identified as a marker for CBC ISCs. (Sato et al., Nature 2009; 459:262-265) Prominin-1 is also expressed in ISC. (Snippert et al., Gastroenterology 2009; 136:2187-2194, Zhu et al., Nature 2009; 457: 603-607).

The integrity of the intestinal epithelium is ensured by pluripotent, self-renewing and proliferative stem cells. Barker et al., Gastroenterology 2007; 133:1755-1760, Potten et al., Cell Prolif 2009; 42:731-750. These cells have only recently been identified using special markers such as Leucine-rich repeat-containing G-protein coupled receptor 5 (LGR5) and prominin-1/CD133, in addition to classic +4 long retention cell characteristics. Barker et al., Nature 2007; 449:1003-1007, Snippert et al., Gastroenterology 2009; 136: 2187-2194. Between 4 and 6 stem cells at each crypt base generate epithelial progenitor cells in the transit-amplifying (TA) zone, which subsequently differentiate and maintain intestinal homeostasis. Barker et al., Gastroenterology 2007; 133:1755-1760, Potten et al., Cell Prolif 2009; 42:731-750. They provide a fast-paced renewal of the four differentiated epithelial cell lineages, each of which has distinct important physiologic functions: enterocytes that absorb nutrients, goblet cells that produce protective mucus, Paneth cells that secrete antibacterial proteins and neuroendocrine cells that produce hormones. Scoville et al., Gastroenterology 2008; 134:849-864. Stresses such as intestinal ischemia can harm the intestinal epithelial cell (IEC) lineages, particularly the stem cells, thereby disrupting normal homeostasis and gut barrier function. Stem cells in some organs, including the intestines, have been shown to respond to stress and to promote recovery from injury. Markel et al., J Pediatr Surg 2008; 43:1953-1963. A previous study showed that bone marrow-derived progenitor cells have the ability to regenerate the intestine after injury. Gupta et al., Biomacromolecules 2006; 7:2701-2709. However, the role of intestinal stem cells (ISCs) in recovery from NEC is unknown. The ability to protect ISCs in the face of stress may represent a critical step in the prevention and treatment of NEC.

Identification of ISCs and their markers is an active area of research. In 1998, a G-protein-coupled receptor with 16 leucine-rich repeats was discovered. Additional leucine-rich G-protein receptors were identified and, ultimately, Hans Clevers of the Hubrecht Institute demonstrated that cells expressing Lgr5, located in the crypt base adjacent to the Paneth cells, are multipotent ISCs [14]. Cell surface markers for ISC include but are not limited to LGR5 and prominin-1 (Barker et al., Nature 2007; 449:1003-1007, Snippert et al., Gastroenterology 2009; 136:2187-2194, Lee et al., Nat Neurosci 2005; 8:723-729, Zhu et al., Nature 2009; 457: 603-607, Chen et al., Growth Factors 2010; 28:82-97).

In the present invention, crypts will be isolated from transgenic Lgr5EGFP mice, and used as cell source of ISC for the regeneration of intestinal epithelium. This protocol will deliver a high percentage of ISC while still maintaining their relationship with mesenchymal cells.

Neural Stem Cells

Neural stem cells (NSCs) are stem cells in the nervous system that can self-renew and give rise to differentiated progenitor cells to generate lineages of neurons as well as glia, such as astrocytes and oligodendrocytes.

NSCs are generated throughout an adult's life via the process of neurogenesis. Since neurons do not divide within the central nervous system (CNS), NSCs can be differentiated to replace lost or injured neurons or in many cases even glial cells. In vivo, NSCs are differentiated into new neurons within the SVZ of lateral ventricles, a remnant of the embryonic germinal neuroepithelium, as well as the dentate gyrus of the hippocampus.

Adult NSCs were first isolated from mouse striatum in the early 1990s. They are capable of forming multipotent neurospheres when cultured in vitro. Neurospheres can produce self-renewing and proliferating specialized cells. These neurospheres can differentiate to form the specified neurons, glial cells, and oligodendrocytes.

Intracelluar markers for NSC include but are not limited to galectin-1, nestin, SOX2. Nestin is expressed predominantly in stem cells of the central nervous system and it is absent from nearly all mature CNS cells. Cell surface markers for NSC include but are not limited to ABCG2, MXR, BCRP, ABCP, FGF R4, Frizzled-9, CD133 and Musashi 1.

Embryonic Stem Cells

Embryonic stem cells (ESC) are derived from embryos that were developed from eggs that have been fertilized using in vitro fertilization. Procedures for isolating and growing human primordial stem cells are described in U.S. Pat. No. 6,090,622. Human embryonic stem cells (hESCs) can be isolated from human blastocysts obtained from human in vivo preimplantation embryos, in vitro fertilized embryos, or one-cell human embryos expanded to the blastocyst stage (Bongso et al., Hum. Reprod. 4:706, 1989). Human embryos can be cultured to the blastocyst stage in G1.2 and G2.2 medium (Gardner et al., Fertil. Steril. 69:84, 1998). The zona pellucida is removed from blastocysts by brief exposure to pronase. The inner cell masses can be isolated by immunosurgery or by mechanical separation, and are plated on mouse embryonic feeder layers, or in an appropriate culture system. Inner cell mass-derived outgrowths are then dissociated into clumps using calcium and magnesium-free phosphate-buffered saline (PBS) with 1 mM EDTA, using dispase, collagenase, or trypsin, or by mechanical dissociation with a micropipette. The dissociated cells are then replated for colony formation. Colonies demonstrating undifferentiated morphology are individually selected by micropipette, mechanically dissociated into clumps, and replated. Embryonic stem cell-like morphology is characterized as compact colonies with apparently high nucleus to cytoplasm ratio and prominent nucleoli.

The ESC may be cultured under conditions that support the substantially undifferentiation growth of the primordial stem cells using any suitable cell culture technique known in the art. For example, the ESCs may be grown on synthetic or purified extracellular matrix using methods standard in the art. Alternatively, the ESC may be grown on extracellular matrix that contains laminin or a growth-arrested murine or human feeder cell layer (e.g., a human foreskin fibroblast cell layer) and maintained in a serum-free growth environment.

Cell surface markers for ESC include, but are not limited to, alkine phosphatase, CD30, Cripto (TDGF-1), GCTM-2, Genesis, Germ cell nuclear factor, OCT-4/POU5F1, SSEA-3, SSEA-4, stem cell factor (SCF or c-kit ligand), TRA-1-60 and TRA-1-81.

Smooth Muscle Cells

Smooth muscle surrounds the supports of many of the hollow organs. For example, in the gut smooth muscle surrounds the stomach and intestinal track. Contraction of this muscle mixes food and propels it along the digestive track. Smooth muscle lacks the nearly uniform cell shape and lattice-like distribution of skeletal and cardiac muscle cells. However, smooth muscle cells do exhibit an elongated, bipolar cell shape. As a population, smooth muscle cells are organized along a similar axis in a series of overlapping cellular layers. This pattern of organization allows smooth muscle to exert contractile forces in a complex pattern.

The present invention can be employed using isolated primary smooth muscle cells or cell lines derived from such primary cells, tumors and the like. For example, cell lines derived from muscle may be obtained from a cell line depository such as the American Type Culture Collection (ATCC, Bethesda, MD). Such cell smooth muscle cell lines include human iliac vein smooth muscle cells (HIVS-125; ATCC accession no. CRL-2482), Syrian Golden Hamster ductus deferens smooth muscle cells (DDT1; CRL-1701), human umbical vein smooth muscle cells (HUVS-112D: CRL-2481), rat aorta smooth muscle cells (Hep-Sa; CRL-2018), and human aortic smooth muscle cells (T/G HA-VSMC; CRL-2498). The conditions for growth of the specific cell line purchased will depend on the biological source and generally instructions for the growth of the cells are made available along with the cell lines from ATCC. Cell surface markers for smooth muscle cells include but are not limited to α-smooth muscle actin, calponin, SM22 and heavy chain myosin,

HB-EGF

The cloning of a cDNA encoding human HB-EGF (or HB-EHM) is described in Higashiyama et al., Science, 251: 936-939 (1991) and in a corresponding international patent application published under the Patent Cooperation Treaty as International Publication No. WO 92/06705 on Apr. 30, 1992. Both publications are hereby incorporated by reference herein in their entirety. In addition, uses of human HB-EGF are taught in U.S. Pat. No. 6,191,109 and International Publication No. WO 2008/134635 (Intl. Appl. No. PCT/US08/61772), also incorporated by reference in its entirety.

The sequence of the protein coding portion of the HB-EGF cDNA is set out in SEQ ID NO: 1 herein, while the deduced amino acid sequence is set out in SEQ ID NO: 2. Mature HB-EGF is a secreted protein that is processed from a transmembrane precursor molecule (pro-HB-EGF) via extracellular cleavage. The predicted amino acid sequence of the full length HB-EGF precursor represents a 208 amino acid protein. A span of hydrophobic residues following the translation-initiating methionine is consistent with a secretion signal sequence. Two threonine residues (Thr75 and Thr85 in the precursor protein) are sites for O-glycosylation. Mature HB-EGF consists of at least 86 amino acids (which span residues 63-148 of the precursor molecule), and several microheterogeneous forms of HB-EGF, differing by truncations of 10, 11, 14 and 19 amino acids at the N-terminus have been identified. HB-EGF contains a C-terminal EGF-like domain (amino acid residues 30 to 86 of the mature protein) in which the six cysteine residues characteristic of the EGF family members are conserved and which is probably involved in receptor binding. HB-EGF has an N-terminal extension (amino acid residues 1 to 29 of the mature protein) containing a highly hydrophilic stretch of amino acids to which much of its ability to bind heparin is attributed. Besner et al., Growth Factors, 7: 289-296 (1992), which is hereby incorporated by reference herein, identifies residues 20 to 25 and 36 to 41 of the mature HB-EGF protein as involved in binding cell surface heparin sulfate and indicates that such binding mediates interaction of HB-EGF with the EGF receptor.

As used herein, "HB-EGF product" includes HB-EGF proteins comprising about amino acid 63 to about amino acid 148 of SEQ ID NO: 2 (HB-EGF(63-148)); HB-EGF proteins comprising about amino acid 73 to about amino acid 148 of SEQ ID NO: 2 (HB-EGF(73-148)); HB-EGF proteins comprising about amino acid 74 to about amino acid 148 of SEQ ID NO: 2 (HB-EGF(74-148)); HB-EGF proteins comprising about amino acid 77 to about amino acid 148 of SEQ ID NO: 2 (HB-EGF(77-148)); HB-EGF proteins comprising about amino acid 82 to about amino acid 148 of SEQ ID NO: 2 (HB-EGF(82-148)); HB-EGF proteins comprising a continuous series of amino acids of SEQ ID NO: 2 which exhibit less than 50% homology to EGF and exhibit HB-EGF biological activity, such as those described herein; fusion proteins comprising the foregoing HB-EGF proteins; and the foregoing HB-EGF proteins including conservative amino acid substitutions. In a specific embodiment, the HB-EGF product is human HB-EGF (74-148). Conservative amino acid substitutions are understood by those skilled in the art. The HB-EGF products may be isolated from natural sources known in the art (e.g., the U-937 cell line (ATCC CRL 1593)), chemically synthesized, or produced by recombinant techniques such as disclosed in WO92/06705, supra, the disclosure of which is hereby incorporated by reference. In order to obtain HB-EGF products of the invention, HB-EGF precursor proteins may be proteolytically processed in situ. The HB-EGF products may be post-translationally modified depending on the cell chosen as a source for the products.

The HB-EGF products of the invention are contemplated to exhibit one or more biological activities of HB-EGF, such as those described in the experimental data provided herein or any other HB-EGF biological activity known in the art. One such biological activity is that HB-EGF products compete with HB-EGF for binding to the ErbB-1 receptor and has ErbB-1 agonist activity. In addition, the HB-EGF products of the invention may exhibit one or more of the following biological activities: cellular mitogenicity, cellular chemoattractant, endothelial cell migration, acts as a pro-survival factor (protects against apoptosis), decrease inducible nitric oxide synthase (iNOS) and nitric oxide (NO) production in epithelial cells, decrease nuclear factor-κB (NF-κB) activation, increase eNOS (endothelial nitric oxide synthase) and NO production in endothelial cells, stimulate angiogenesis and promote vasodilatation.

The present invention provides for the HB-EGF products encoded by the nucleic acid sequence of SEQ ID NO: 1 or fragments thereof including nucleic acid sequences that hybridize under stringent conditions to the complement of the nucleotides sequence of SEQ ID NO: 1, a polynucleotide which is an allelic variant of any SEQ ID NO: 1; or a polynucleotide which encodes a species homolog of SEQ ID NO: 2.

Expression of HB-EGF by Cells within the Construct

The invention provides for transforming or transfecting somatic stem cells, such as MSC, NSC and ISC, and/or SMC with a nucleic acid encoding the amino acid sequence of a HB-EGF product. The transformed somatic stem cells are then administered to a patient suffering from an intestinal injury in any of the methods of the invention which results in administration of the HB-EGF product and the somatic stem cell concurrently.

A nucleic acid molecule encoding the amino acid sequence of an HB-EGF product may be inserted into an appropriate expression vector that is functional in stem cells using standard ligation techniques. Exemplary vectors that function in somatic stem cells include bacterial vectors, eukaryotic vectors, plasmids, cosmids, viral vectors, adenovirus vectors and adenovirus associated vectors.

The expression vectors preferably may contain sequences for cloning and expression of exogenous nucleotide sequences. Such sequences may include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element.

The vector may contain a sequence encoding a "tag", such as an oligonucleotide molecule located at the 5' or 3' end of the HB-EGF product coding sequence; an oligonucleotide sequence encoding polyHis (such as hexaHis), FLAG, hemaglutinin influenza virus (HA) or myc or other tags for which commercially available antibodies exist. This tag may be fused to the HB-EGF product upon expression. A selectable marker gene element encoding a protein necessary for the survival and growth of a host cell grown in a selective culture medium may also be a component of the expression vector. Exemplary selection marker genes include those that encode proteins that complement auxotrophic deficiencies of the cell; or supply critical nutrients not available from complex media.

A leader, or signal, sequence may be used to direct the HB-EGF product out of the stem cell after administration. For example, a nucleotide sequence encoding the signal sequence is positioned in the coding region of the HB-EGF product nucleic acid, or directly at the 5' end of the HB-EGF coding region. The signal sequence may be homologous or heterologous to the HB-EGF product gene or cDNA, or chemically synthesized. The secretion of the HB-EGF product from the stem cell via the presence of a signal peptide may result in the removal of the signal peptide from the secreted HB-EGF product. The signal sequence may be a component of the vector, or it may be a part of the nucleic acid molecule encoding the HB-EGF product that is inserted into the vector.

The expression vectors used in the methods of the invention may contain a promoter that is recognized by the host organism and operably linked to the nucleic acid sequence encoding the HB-EGF product. Promoters are untranscribed sequences located upstream to the start codon of a structural gene that control the transcription of the structural gene. Inducible promoters initiate increased levels of transcription from DNA under their control in response to some change in culture conditions, such as the presence or absence of a nutrient or a change in temperature. Alternatively, constitutive promoters initiate continual gene product production with little or no control over gene expression. A large number of promoters, recognized by a variety of potential host cells, are well known. A suitable promoter is operably linked to the nucleic acid molecule encoding the HB-EGF product. The native HB-EGF gene promoter sequence may be used to direct amplification and/or expression of a HB-EGF product nucleic acid molecule. A heterologous promoter also may be used to induce greater transcription and higher yields of the HB-EGF product expression as compared to HB-EGF expression induced by the native promoter.

In addition, an enhancer sequence may be inserted into the vector to increase the transcription of a DNA encoding the HB-EGF product. Enhancers are cis-acting elements of DNA, usually about 10-300 bp in length, that act on the promoter to increase transcription. Enhancer sequences available from mammalian genes include globin, elastase, albumin, alpha-feto-protein and insulin. Exemplary viral enhancers that activate eukaryotic promoters include the SV40 enhancer, the cytomegalovirus early promoter enhancer, the polyoma enhancer, and adenovirus enhancers. While an enhancer may be spliced into the vector at a position 5' or 3' to a nucleic acid molecule encoding the HB-EGF product, it is typically located at a site 5' from the promoter.

The transformation of an expression vector encoding a HB-EGF product into a stem cell may be accomplished by well-known methods such as transfection, infection, calcium chloride, electroporation, microinjection, lipofection or the DEAE-dextran method or any other technique known in the art. These methods and other suitable methods are well known in the art, for example, in Sambrook, Molecular Cloning: A Laboratory Manual, Cold Spring Harbor Laboratory Press; 3rd ed., 2001.

BRIEF DESCRIPTION OF DRAWING

FIG. 2A is a schematic of scaffold orientation in vivo. FIG. 2B) depicts the abdominal wall after harvesting at 4 weeks showing scaffolds secured in their location against the underside of the abdominal wall. Poly(glycolic acid)-macrofiber (PGA-M), Poly(glycolic acid)-nanofiber (PGA-N), Poly(-caprolactone-co-lactic acid)-nanofiber (PLC-N), Poly(-caprolactone)-nanofiber (PCL-N), Poly(D-lactic acid-co-glycolic acid) (PDLGA-N) Poly(L-lactic acid)-nanofiber (PLLA-N), and Polyurethane-nanofiber (PU-N).

FIGS. 3A-3N depicts histologic examination of scaffolds. Representative photomicrographs of FIG. 3H & FIG. 3E stained sections of each of the 7 scaffolds FIGS. 3A-3G) 1 week and FIGS. 3H-3N) 4 weeks after implantation. FIG. 3A and FIG. 3H) PGA-nanofiber: significant tissue infiltration begins at 1 week and no fibers are visible at 4 weeks; FIG. 3B and FIG. 3I) PGA-macrofiber: significant tissue infiltration is visible starting at 1 week; some fibers remain visible at 4 weeks; FIG. 3C and FIG. 3J. PCL-nanofiber: significant tissue infiltration and retained fiber structure are visible at 4 weeks; FIG. 3D and FIG. 3K) PLC-nanofiber: minimal tissue infiltration and minimal degradation; FIG. 3E and FIG. 3L) PLLA-nanofiber: almost no tissue infiltration and minimal degradation; FIG. 3F and FIG. 3M) PDLGA-nanofiber: less tissue infiltration at 1 week but rapid degradation by 4 weeks; FIG. 3G and FIG. 3N. PU-nanofiber: some tissue infiltration and no fiber degradation at 4 weeks.

FIGS. 5A-5N provides scanning electron microscopic examination of scaffolds. SEM images (500×) of scaffolds FIGS. 5A-5G) prior to implantation and FIGS. 5H-5N) 4 weeks days after implantation. FIGS. 5A and 5H) PGA-nanofiber; FIG. 5B and FIG. 5I) PGA-macrofiber; FIG. 5C and FIG. 5J) PCL-nanofiber; FIG. 5D and FIG. 5K) PLC-nanofiber; FIG. 5E and FIG. 5L) PLLA-nanofiber; FIG. 5F and FIG. 5M) PDLGA-nanofiber; and FIG. 5G and FIG. 5N) PU-nanofiber. Insets show gross scaffold appearance.

FIG. 6A) ultimate tensile strength; FIG. 6B) percent elongation; FIG. 6C) Young's modulus. SB, small bowel; M, macrofiber; N, nanofiber.

FIGS. 8A-8D depict the filtration system used to enrich intestinal stem cells in crypts. This system consists of a bottom filter, top cups, sieve membranes, and cell scraper (FIG. 8A). The smallest size (8 μm) has been loaded first and placed on the top of base filter cup (FIG. 8B). The second top cup has been placed on the base filter cup to secure the sieve membrane (FIG. 8C). Similarly, all other sizes of sieve membranes have been loaded in order from smaller to larger pore sizes, and a vacuum tube is connected FIGS. 9A-9F depict localization of ISC in filtered fractions.

FIGS. 10A-D depict the appearance of TEI produced from ISC-enriched compared to non-enriched seeding.

DETAILED DESCRIPTION

Example 1 describes the preliminary studies that analyzed different scaffold materials. Example 2 describes scaffold fabrication. Example 3 describes in vitro characterization of the nanofiber scaffolds. Example 4 describes cell seeding of the nanofiber scaffolds and Example 5 describes biological characterization of nanofiber scaffolds. Example 6 describes a cell filtration system to enrich intestinal stem cells in crypts. Example 7 describes HB-EGF incorporation into PGA enhances the formation of tissue engineered intestine.

EXAMPLES

Example 1

Analysis of Scaffold Materials

This detailed evaluation of the numerous potential scaffold materials was carried out to determine potential scaffold materials for the construction of a multilayer nanofiber scaffold for use in generating engineered intestine constructs. The purpose of this study was to characterize seven different scaffold materials according to degradation rates, histologic changes, and tensile strength to determine which would be best suited for the production of the engineered intestine constructs.

Initially, the seven different single tube scaffolds were fabricated using electrospinning as described in Example 2 and above. These scaffolds were comprised of poly(glycolic acid)(PGA) nanofibers, Poly(-caprolactone) (PCL) nanofibers, Poly(-caprolactone-co-lactic acid) (PLC) nanofibers, Poly(L-lactic acid) (PLLA), Poly(D-lactic acid-co-glycolic acid) (PDLGA), Polyurethane (PU) nanofibers and PGA macrofibers. The physical and chemical characteristics of the nanofiber scaffolds are provided in Table 2.

TABLE 2

Characteristics of Polymers

| Polymer | Molecular Formula | Density (g/cm$^3$) | Melting point | Tensile modulus of elasticity (GPa) | Tensile strength (MPa) | Elongation at break (%) | Degradation time (months) |
|---|---|---|---|---|---|---|---|
| PGA | $(C_2H_2O_2)_n$ | 1.5 | 225-230° C. | 6.5-7.0 | 90-110 | 1-2 | 6-12 |
| PCL | $(C_6H_{10}O_2)_n$ | 1.2 | 60° C. | 0.2-0.3 | 25-35 | >300 | >24 |
| PLC | $((C_3H_4O_2)\text{—}(C_6H_{10}O_2))_n$ | 1.25 g/cm$^3$ | 110-120° C. | 0.02-0.04 | 18-22 | >100 | 12-24 |
| PLLA | $(C_3H_4O_2)_n$ | 1.3 | 150-160° C. | 3.1-3.7 | 60-70 | 2-6 | >24 |
| PDLGA | $((C_3H_4O_2)\text{—}(C_2H_2O_2))n$ | 1.4 | amorphous | 3.4-3.8 | 40-50 | 1-4 | 1-2 |
| PU | $((C_{16}H_{14}O_3)_x\text{—}(C_{15}H_{14}O_2))_n$ | 1.2 | 180° C. | 0.03 | 45-50 | >500 | biostable |

Figure 1:
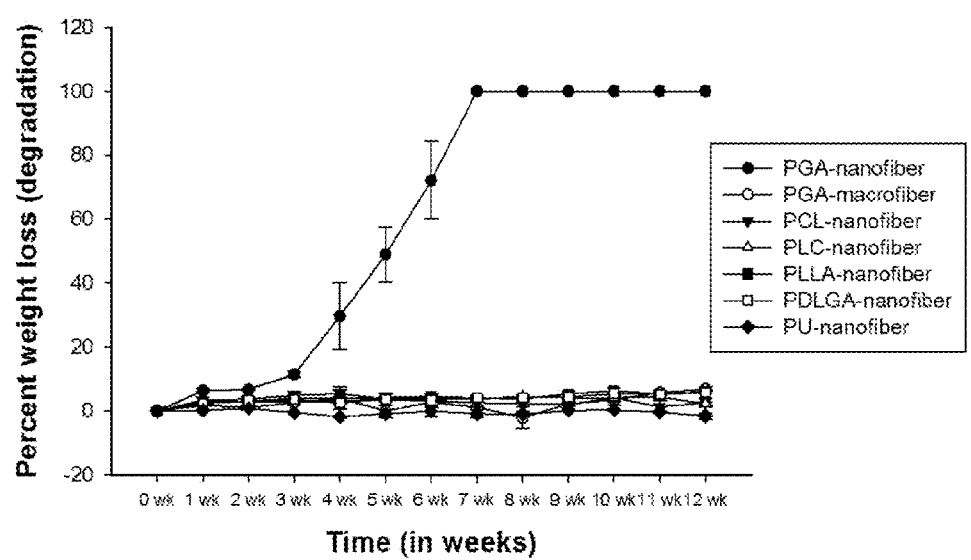
FIG. 1 depicts in vitro degradation rate. The percent of weight loss for each scaffold over 12 weeks of incubation in stimulated intestinal fluid. Only PGA-nanofiber displays significant weight loss over this period.

Prior to implantation, the in vitro degradation of the scaffolds was analyzed in simulated intestinal fluid (SIF). The degradation rate of each scaffold type was assessed by weekly measurements of change in scaffold weight over the 12-week incubation period. The PGA-nanofiber was the only composition that underwent significant, measurable change and showed complete degradation by week 8. All other materials displayed little weight change. Several of the weekly measurements suggested a slight weight gain (see FIG. 1). This was attributable to solute from SIF solution that remained trapped in the nanoscaled scaffold even after multiple rinses.

In Vivo Studies

The scaffolds were sterilized and maintained at −20° C. until implantation. PGA-nanofiber, PGA-macrofiber, PLLA-nanofiber and PU-nanofiber scaffolds were sterilized via exposure to hydrogen peroxide gas (Sterrad). PC-nanofiber and PLC-nanofiber scaffolds were sterilized via immersion in 70% ethanol solution for 30 minutes. The sterilized scaffolds were implanted onto the interior surface of the abdominal wall of adult Lewis rats.

Figure 2A:
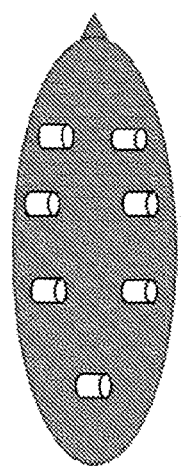
FIGS. 2A-2B depicts the scaffold implantation in vivo.
Figure 2B:
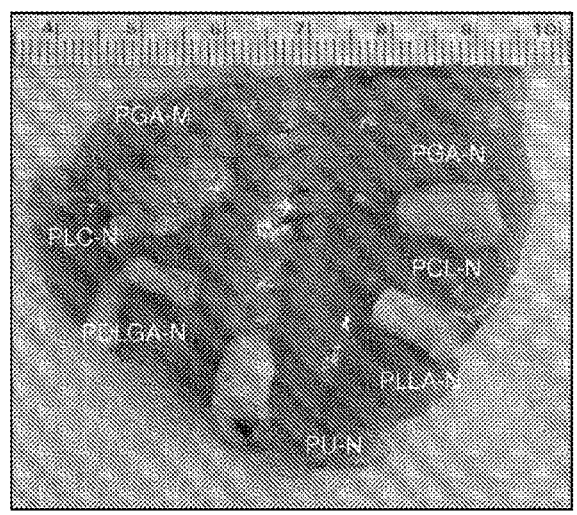

Under general anesthesia with inhalation of isofluorane, a midline laparotomy was performed and a 1 cm length of each of the seven scaffolds was secured to the anterior abdominal wall of the peritoneal cavity using 5-0 polypropylene suture. Three scaffolds were placed on either side of the midline and one in the pelvis (FIG. 2A). Each scaffold was secured with two 5-0 polypropylene sutures passed through the lumen of the scaffold and then secured to the fascia. Animals were euthanized by $CO_2$ asphyxiation and scaffolds harvested at each of 6 time points (1, 2, 3, 4, 8 and 12 weeks) (Figure) were used for histological evaluation (n=3), weight changes and SEM examination (n=3).

Upon harvesting, these scaffolds were also tested for ultimate tensile strength, elongation, and modulus. Modulus (Young modulus) was measured as the ratio of the uniaxial stress over the uniaxial strain in the range of stress in which Hooke's Law holds. Elongation was measured as the percentage of original dimensions. Furthermore, ultimate tensile strength (UTS) was measured within the limitations inherent to standard tensile evaluation of component properties at these scales.

Histology

The scaffolds were subjected to H&E staining and examined histologically at 1 week and 4 weeks after implantation. Scaffolds were harvested en bloc, cut in a cross-sectional fashion across the center of the scaffold, fixed in 10% neutral buffered formalin and embedded in paraffin. Three sections were obtained from each of three levels at 200 μm intervals, deparaffinized in Americlear (Cardinal Health, Dublin, OH), and stained with hematoxylin and eosin (H&E) dye. Slides were examined and assessed microscopically. The histologic examination is depicted in FIGS. 3A-3N.

Histologically, PGA-nanofiber scaffolds had both significant tissue infiltration as well as fiber degradation at early time points (1 and 2 weeks) with no fibers left at 4 weeks. There was marked tissue reaction with granulomatous inflammation at 2 weeks post-implantation, with numerous macrophages and a few foreign body giant cells. A reduction in the inflammatory reaction was observed, as the fibers were absorbed at 4 weeks post-implantation.

PGA-macrofiber scaffolds also had significant tissue infiltration at early time points, but maintained structural integrity longer (some fibers still visible at 4 weeks). Fiber degradation was observed beginning at 21 days post-implantation. There was marked foreign body reaction at 2 weeks post-implantation again characterized by numerous foreign body giant cells and macrophages. Fibrosis located within the midpoint of the scaffold wall was observed at 2 weeks.

PCL-nanofibers had slower tissue infiltration that became more prominent at 2 to 3 weeks, and maintained structural integrity after 4 weeks. PLC-nanofibers had minimal degradation and poor tissue infiltration. There was foreign body reaction by 2 weeks post-implantation and fibrosis was observed starting at 3 weeks, and remained visible up to 12 weeks post-implantation.

PLC-nanofiber scaffolds showed poor tissue infiltration. The tissue reaction was characterized generally by chronic inflammation and fibrosis. Mild chronic inflammation was also present at 4, 8 and 12 weeks.

PLLA also had slower tissue infiltration that did not occur until at least 3 weeks post-implantation. The tissue reaction was characterized by mild chronic inflammation present throughout all time points; marked fibrosis was observed beginning at 3 weeks post-implantation. Fibers remained visibly intact up to 12 weeks post-implantation.

PDLGA-nanofibers underwent slightly slower tissue infiltration (present at 2 weeks) but rapid structural loss at 3 to 4 weeks. The tissue reaction was characterized by inflammation and fibrosis, both of which were mild at 1-2 weeks post implantation and more chronic at 3-4 weeks. This was followed by a reduction in the inflammatory reaction as fibers were absorbed beginning at 4 weeks post-implantation. Degradation of fibers was visible at 1 week; fibers were essentially completely absorbed by 4 weeks post-implantation.

PU-nanofibers had tissue infiltration at 3 to 4 weeks but maintained structural integrity at all time points. The tissue reaction was characterized generally by chronic inflammation and fibrosis. The chronic tissue reaction transitioned to a foreign body reaction and fibrosis at 4 weeks post-implantation. Visibly undamaged fibers were present up to 12 weeks post-implantation.

In Vivo Degradation After Peritoneal Implantation

In addition, PGA-macrofiber and PDLGA caused the least amount of tissue reaction at and around the implant sites compared to the other materials. Scaffolds were cut into 4-6 pieces and placed into 4 ml of 5% sodium hypochlorite (Sigma-Aldrich, St Louis, MO) diluted with phosphate buffered saline (PBS), to remove in-growth tissues. After digestion of adherent biological tissue in sodium hypochlorite, the scaffolds were rinsed five times in distilled water and freeze dried overnight. Each sample was then weighed to determine the amount of scaffold degradation as assessed by the change in weight pre-implantation. Each of the seven scaffold materials were examined in triplicate at each time point and the percentage of weight loss calculated.

Figure 4:
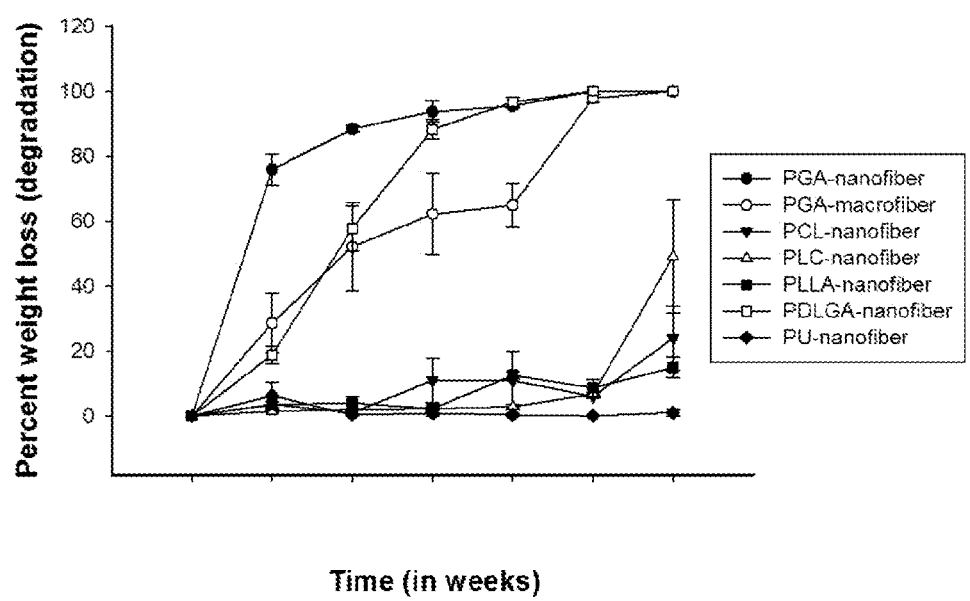
FIG. 4 depicts in vivo degradation rate, Weight loss over a 12 week incubation period after intra-peritoneal implantation. Both the PGA and PDLGA nanofiber as well as the PGA macrofiber display significant weight loss over the period.

Significant weight loss was identified for PGA-nanofiber (92.2%±9.3%), PGA-macrofiber (67.6%±28.8%), and PDLGA 76.9%±31.0%) scaffolds as opposed to PU-nanofiber (1.5%±3.4%%), PCL-nanofiber (10.7%±20.6%%), PLC-nanofiber (9.4%±11.8%) and PLLA-nanofiber (7.6%±5.7%) (all with p<0.05) when combining the percent weight loss for scaffolds at all time pointes. See FIG. 4. In addition to having significantly higher weight loss, PGA-nanofiber, PDLGA-nanofiber, and PGA-macrofiber had the bulk of the weight loss during the earlier time points, when compared to the other scaffold materials.

Scanning Electron Microscopy (SEM)

Scanning electron microscopy was also performed for each of the scaffolds at each time point. See FIGS. 5A-5N. Individual fibers were indistinguishable for all PLC scaffolds, for PGA-nanofiber scaffolds after 1 week, for PGA-macrofiber scaffolds at 2 weeks, and for PDLGA-nanofiber scaffolds at 4 weeks. Little change in fiber size, structure, or pore size was seen in PCL-nanofiber, PLLA-nanofiber and PU-nanofiber scaffolds. PDLGA-nanofiber scaffolds underwent significant microstructural changes including increased pore size and individual fiber breakage at 2 weeks.

The percent weight loss compared to the baseline weight of each of the seven scaffolds at 1 week, 2 weeks, 3 weeks, 4 weeks, 8 weeks and 12 weeks is determined from e SEM images. A portion of each of the samples used for scaffold degradation studies was gold sputtuer-coated (Emitech K550X, Quorum Technologies Ltd, Ashford, Kent, England) and examined by SEM (Hitachi S-4800, Hitachi High Technologies Americca, Inc., Dallas, TX) at a voltage of 7 kV at 100, 500, and 1000× magnification. Measurements of fiber diameter were taken from the SEM micrographs at random locations at 500× magnification using Image J software (National Institutes of Health, Bethesda, MD) from three different scaffold samples representing each time point. PGA-nanofiber had the most rapid degradation, followed by PGA-macrofiber and PDLGA-nanofiber. PCL-nanofiber, PLC-nanofiber, PLLA-nanofiber had much slower degradation. PU-nanofiber had no significant degradation even at 12 weeks.

SEM was performed for each of the scaffolds at each time point. Fiber width was measured from SEM images. Individual fibers were not distinguished for PLC-nanofiber scaffolds at any time, PGA-nanofiber at 1 week, PGA-macrofiber at 2 weeks, and PDLGA-nanofiber at 4 weeks. Little change in fiber size, structures, or pore size was seen in PCL-nanofiber, PLLA-nanofiber and PU-nanofiber scaffolds. PGA-macrofiber had an increase in fiber size at 3 weeks followed by subsequent decline. PDLGA-nanofiber scaffolds underwent significant changes including increased pore size and individual fiber breakage at 2 weeks.

Tensile Strength

Figure 6A:
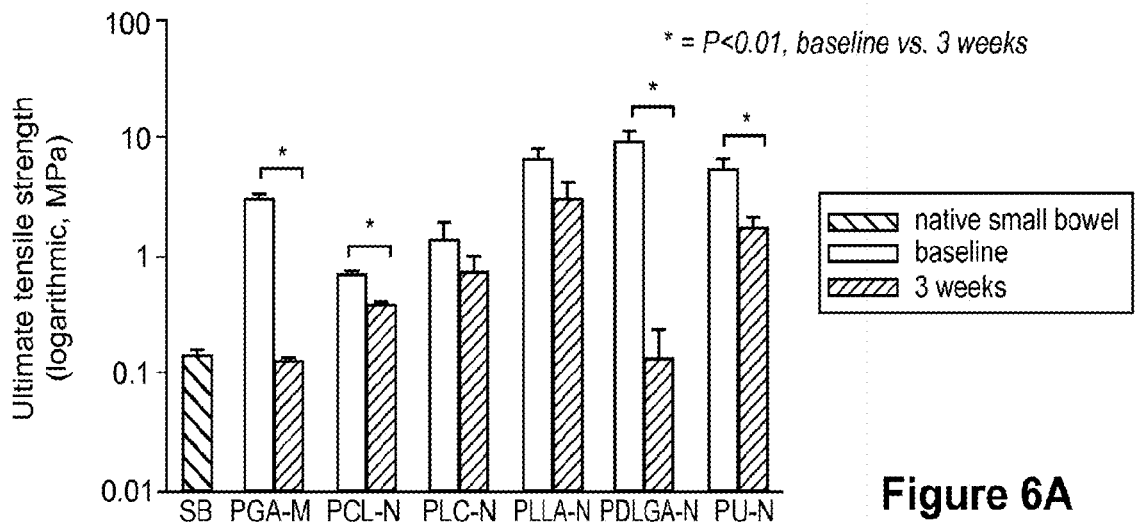
FIGS. 6A-6C depict tensile strength measurements for native small bowel, and for scaffolds both prior to and after 3 weeks of implantation.
Figure 6B:
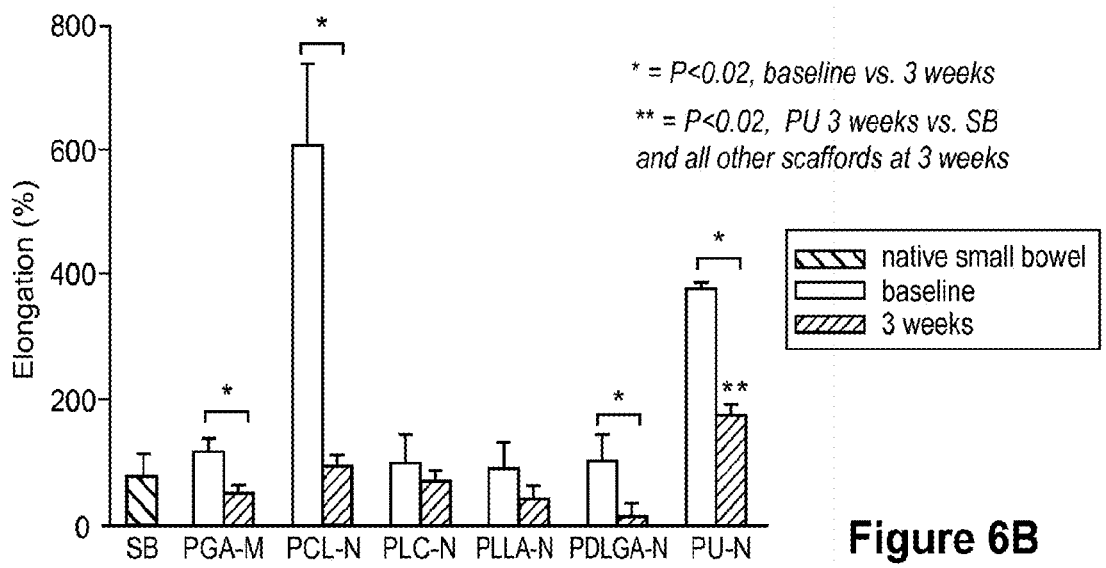
Figure 6C:
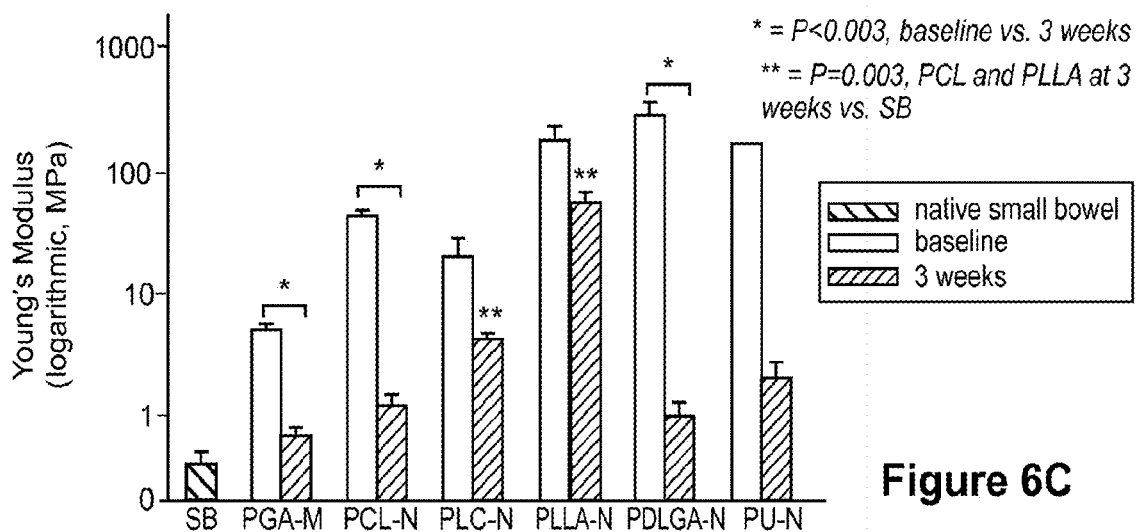

Tensile strength measurements were taken for native small intestine, as well as for each of the six scaffold materials (PGA-macrofiber, PCL-nanofiber, PLLA-nanofiber, and PU-nanofiber) at baseline and after 3 weeks of intra-abdominal implantation (FIGS. 6A-6C) and after 3 weeks of intra-abdominal implantation (FIG. 6A-6C). PGA-nanofiber scaffolds were not used for testing of tensile strength due to near complete degradation at the 3 week time point. There is a statistically significant reduction in ultimate tensile strength (UTS) after implantation compared to baseline for PGA-macrofiber (p<0.001), PCLnanofiber (p=0.001), PDLGA-nanofiber (p<0.001), and PU-nanofiber (p=0.01). There was also a statistically significant reduction in percent elongation after implantation compared to baseline for PGA-macrofiber (p=0.002), PCL-nanofiber (p=0.003), PDLGA-nanofiber (p=0.018), and PU-nanofiber (p<0.001). There was a statistically significant reduction in Young's modulus after implantation compared to baseline for PGA-macrofiber (p<0.001), PCL-nanofiber (p<0.001), and PDLGA-nanofiber (p=0.003).

Ultimate tensile strength is the highest point on the stress-strain curve, and represents the maximum amount of stress that a material can withstand before breaking or failing. Young's modulus, on the other hand, is the linear portion of the stress-strain curve, and corresponds to the ability of the scaffold to withstand alterations in length when exposed to tension. These factors are critical to the evaluation of our scaffolds as they determine how the scaffold would respond to a bolus of food or peristalsis compared to the surrounding native small bowel. It has been shown that deposited ECM and tissue infiltration can have significant effects on the tensile properties of these nanofiber scaffolds (Johnson et al., J. Appl. Polymer Sci. 104(5):2919-2927, 2007; Johnson et al., J. Biomat. Sci.—Polymer Ed. 20(4): 467-481, 2009). The mechanical response of the scaffolds depends upon the rearrangement and alignment of the nanofibers in the direction of strain and the biological milieu can prohibit that fiber rearrangement.

In terms of tensile strength and suture retention testing, all scaffolds initially displayed equal or better strength and suture retention strength (see below) than the native small bowel. PLLA-nanofiber and PDLGA-nanofiber were much stiffer than the other scaffolds. The percent elongation was not statistically different as compared to the small bowel due to the relatively low strength of the small bowel compared to the PLLA-nanofiber and PDLGA-nanofiber scaffolds. This lack of stiffness has some benefit, however, in that it can help to maintain structural architecture during the formation of new tissues (Lee et al., Biomed. Mater. 8(1): 0101201, 2012). After 3 weeks of implantation, PGA-macrofiber and PDLGA-nanofiber most closely resembled the mechanical characteristics of small intestine, with PCL-nanofiber being the next closest in regards to mechanical characteristics of the small intestine.

In addition, the mechanical properties of native small intestine were compared to each of the scaffolds at 3 weeks; no statistically significant differences in UTS were apparent. There was a statistically significant difference between percent elongation and PU-nanofiber compared to native small bowel, as well as each of the other 5 scaffolds (p<0.03), but no significant differences between the other scaffolds and the native small bowel. PLLA-nanofiber and PLC-nanofiber had significantly higher Young's modulus when compared to native small bowel (p=0.003), but no other significant differences could be identified.

Suture Retention

Figure 7:
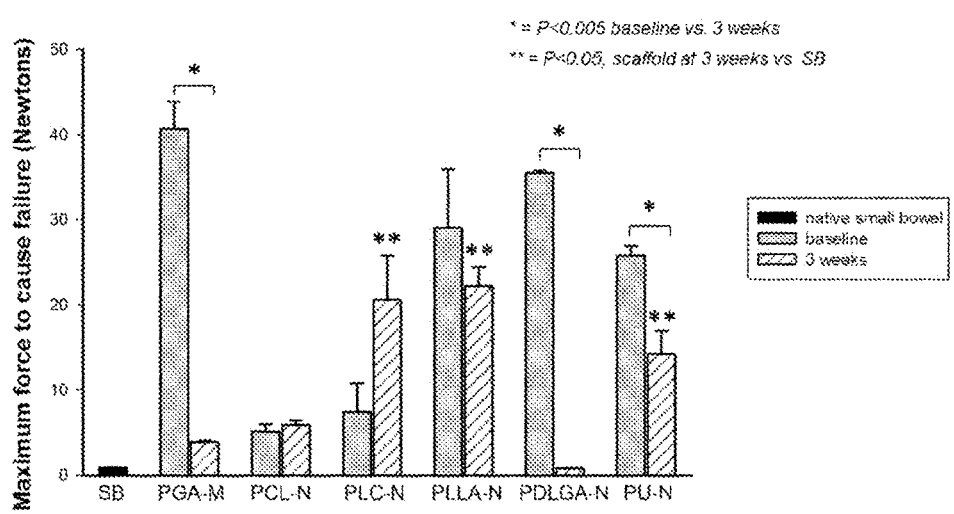
FIG. 7 depicts suture retention strength of the implanted scaffolds. Suture strength measurements (in Newtons) for native small bowel and for scaffolds prior to and after 3 weeks of implantation. SB, small bowel; M, macrofiber; N, nanofiber.

Suture retention strength (SRS) was evaluated for native small intestine and each of 6 scaffolds at baseline and after 3 weeks of intra-abdominal implantation (FIG. 7). PGA-nanofiber scaffolds were not used for SRS testing due to nearly complete degradation at the 3-week time point. Maximum force was calculated in Newtons for the small intestine samples as well as for each of the samples. There was a statistically significant reduction in SRS after 3 weeks of implantation for PGAmacrofiber ($p<0.001$), PDLGA-nanofiber ($p<0.001$), and PU-nanofiber ($p=0.02$).

The maximum force for each scaffold after 3 weeks of implantation was also compared to that of the small intestine samples. PLC-nanofiber, PLLA-nanofiber, and PU-nanofiber all had significantly higher SRS than native small bowel following 3 weeks of intra-abdominal implantation ($p<0.05$ for each). There was no statistically significant difference between native small intestine and the other 3 scaffolds after 3 weeks of implantation (PGA-macrofiber, PCL-nanofiber, and PDLGA-nanofiber) (FIG. 7).

This analysis of the seven scaffolds indicated that PGA-macrofiber and PDLGA appear to be the most appropriate scaffolds for the production of tissue engineered intestine due to their degradation in approximately 3 weeks and their biocompatibility.

In this specific environment, the PDLGA-nanofiber and PLLA-nanofiber scaffolds appear to strike the appropriate balance of properties needed to maintain structural integrity while allowing for the appropriate rate of tissue replacement of the synthetic scaffold. However, PDLGA-nanofiber appeared to be more biocompatible displaying a minimal foreign body response and a more ideal degradation rate. PU-nanofiber and PLC-nanofiber are much less ideal in this context due to their longer degradation rates, decreased porosity, and ongoing foreign body response. PCL-nanofiber causes significant tissue reaction but slower degradation making it appear less ideal. PGA-nanofiber scaffolds degraded too rapidly and did not allow sufficient ECM production, making it difficult to completely assess the state of the scaffold, as we were unable to test the characteristics of this scaffold. Finally, PGA-macrofiber causes significant tissue reaction but does have a more ideal degradation rate and tensile strength compatible with the production of TEI.

Example 2

Scaffold Fabrication

A multilayer nanofiber scaffold was fabricated for generation of an engineered intestine constructs. Multilayer scaffolds were constructed in order to facilitate the delivery of cells of different sizes, e.g. neural stem cells, smooth muscle cells and crypt cells. In addition, the multilayer scaffold allows for different mechanical properties within the scaffold, allows for a smooth lumen and allows for separation of different cell types which allowed for the generation of different types of tissue.

To seed the scaffolds with cells, the scaffolds are coated onto a cell culture plate for three dimensional cell culture. Human smooth muscle cells are plated and within these cultures the cells migrated along the nanofibers after 5 days in culture. The migration of the smooth muscle cells (SMC) demonstrates that upon seeding of smooth muscle cells into a circumferentially or longitudinally aligned nanofiber tubular layer, the SMCs will align, orientate, migrate, and proliferate along the nanofibers to form muscularis interna and externa. Tubular nanofiber scaffolds are fabricated with PCL and have similar physical properties to native. By controlling the size of the fibers and pores, cell clusters (crypts) as well as individual cells can be seeded on separate layers.

Based on the modulus test described above and in vitro and in vivo degradation studies PGA-macrofiber and PDLGA are good polymers for fabrication of electrospun multilayer nanofiber scaffold. An exemplary multilayer nanofiber scaffold structure is as follows: outer layer of PDLGA, a layer of PCL, a middle layer of PDLGA, a layer of macrofiber PGA and an internal layer of PDLGA.

Polymer solutions were prepared by dissolving polymers in an optimal amount of organic solvent mixture and mixing by a magnetic stir bar overnight (12 hours). The solvent type used and the concentration of each polymer solution prepared for electrospinning were optimized to achieve the desired fiber diameter and scaffold porosity in order to promote cell attachment and infiltration through the scaffold. A pore size gradient was applied through the sidewall starting from the innermost layer with the biggest pores (100-300 pm) and ending at the outermost layer with the smallest pores (50-100 pm). This pore size gradient is designed for loading crypts (cell clusters) and a mixture of MSCs and NSCs separately in order to generate mucosa internally surrounded by smooth muscle/ENS externally.

Briefly, a 5 wt % solution of biodegradable polymer, such as PDLGA, PLC or PCL in 1,1,1,3,3,3-Hexafluoro-2-propanol (HFIP), was prepared by continuous stirring at room temperature overnight to dissolve the polymer. This solution was then placed in a 60 ml syringe with a 20 gauge blunt tip needle and electrospun using a high voltage DC power supply (Glassman High Voltage, Inc., High Bridge, NJ) set to +16 kV, a 20 cm tip-to-substrate distance and a 5 ml/hr flow rate. The fiber was deposited onto a rotating 4.76 mm diameter stainless steel rod until the desired wall thickness was achieved. The arrangement of fibers was controlled as nonwoven in the innermost layer, circumferential alignment in the middle layer, and longitudinal alignment in the outermost layer, in order to recapitulate the natural alignment of native intestinal smooth muscle layers. The thickness ratio of the three layers was 100 pm (outer layer), 200 pm (middle layer), and 200 pm (inner layer) for a total sidewall thickness of 0.5 mm, based on the anatomic structure of native intestine. The scaffold tubes were then removed from the rod, heated, and placed under vacuum to ensure removal of residual organic solvent. Finally, the scaffold tubes were plasma treated, which increases the surface energy and promotes cellular attachment to the fibers.

HB-EGF is a potent intestinal protective agent that promotes intestinal epithelial cell (IEC) and SMC proliferation and migration. Therefore, to accelerate and mature tissue formation in vitro and in vivo, HB-EGF was embedded on the scaffold nanotubes via subcritical $CO_2$ infusion. The dose of HB-EGF to be used for each 5 cm long scaffold was calculated based on the dosages per surface area efficacious in our multiple animal models of intestinal injury. For example, 40 pg of HB-EGF is typically administered enterally to rat pups over five days, with an average length of intestine of 18 cm and diameter of 2 mm. This equates to a dose of HB-EGF per surface area of 1.77 $pg/cm^2$, which is equivalent to 15.7 pg of HB-EGF in a 5 cm long scaffold tube. These amounts were used as a reference range for the coating of scaffold tubes. Different scaffold tubes are uniformly hydrated with 1, 10, or 100 pg of HB-EGF in DPBS buffer and then placed into a chamber in which the pressure is maintained at 900 psi via 002 for 1 hour followed by gradual pressure release at 90 psi per minute. HB-EGF-embedded compared to non-HB-EGF-embedded scaffolds then underwent in vitro and in vivo characterization.

Example 3

In Vitro Characterization of the Nanofiber Scaffolds

A total of seven nanofiber scaffolds (PCL, PLC, PCL-FHB-EGF, PLC-FHB-EGF) are fabricated as described in Example 1 and each of these scaffolds are analyzed using the following in vitro characterizations. Any nanofiber scaffold of the invention will be characterized using one or more of the following analyses.

Scanning Electron Microscopy (SEM)

Scaffolds are sputter coated with gold and then observed under a scanning electron microscope at an accelerated voltage of 15 kV. Fiber and pore size of the inner and outer layers are measured using Image J software and continuity between pores are assessed. Fiber and pore size between HB-EGF-coated and noncoated scaffolds are compared using Student t-test, with $p<0.05$ considered statistically significant. The scanning electron microscopy studies provide guidance on how modify the fiber size and pore size to best accommodate the cells to be seeded into the scaffold.

Modulus Determination

Tensile properties are determined utilizing a 1-kg load cell (Model 31, Sensotec) and a strain rate of 50 mm/min on an Instron load frame using a lightweight carbon fiber. The nanofiber tubes are cut into 5 cm lengths, and the same lengths of rat intestine are prepared. Grips will be modified to incorporate 80-grit sandpaper affixed with heavy-duty double-sided tape to securely fix scaffold tubes during tensile testing. All scaffolds are weighed and their width and thickness in flat state measured with a digital micrometer prior to testing. After mounting, the gauge length of samples are measured and a small tare load applied (−0.05 lbs) to ensure proper seating. Ten sinusoidal pre-conditioning cycles are then carried out to 1% of the gauge length at a strain rate of 0.1%/s. After pre-conditioning, a constant strain of 0.1%/s will be applied until sample failure or 50% strain are achieved. In cases where samples do not fail, the non-recoverable deformation will be assessed by releasing the applied deformation until the measured load becomes negligible at equilibrium. The Young's modulus of samples in tension are calculated from the slope of the stress-strain curve in the linear region (i.e., below the yield stress) and the initial sample geometry. Yield stress and yield strain for each sample are determined from the intersection of the experimental data with a line parallel to the linear region of the stress strain curve and offset by +0.2% strain. Comparisons between the nanofiber scaffolds and native intestine are conducted using one-way ANOVA, with $p<0.05$ considered statistically significant.

Suture Retention Strength

Suture retention strength (SRS) are used to measure the force necessary to pull sutures through the wall of the material being tested. Nanofiber scaffolds and rat intestine (n=5 each) are cut into 5 cm lengths, and three silk sutures (6.0 Ethicon with a cutting edge needle) are inserted 2 mm from the end at 90° angles, looped, and tied with seven knots. The suture loop and the other end of the tube are secured to the grips of the tensile machine using a 22.7-kg (50 lbs) load cell and pulled at 50 mm/min until the suture pulls through the sample wall. The maximum force required is the SRS. Comparisons between nanofiber scaffolds and native intestine are conducted using one-way ANOVA, with $p<0.05$ considered statistically significant.

Degradation in Simulated Intestinal Fluid (SW)

In vitro degradation studies in simulated intestinal fluid are conducted in 2 ml filter tubes with 0.22 μm pore size filters at the bottom. Nanofiber scaffolds are cut into 0.5 cm segments and the outside diameter and sidewall thickness are measured and recorded. Segments of each material area added into individual tubes followed by the addition of 1.8 ml of SIF, which is prepared according to US Pharmacopeia. Tubes are mounted on a rotating system and were kept rotating for 1 hour. The SIF is completely removed, and the tube together with the scaffold were weighed, which is used as the Day 0 baseline weight. After all samples are weighed, 1.8 ml of fresh SIF are added to each tube followed by continuous rotating until the next time point of sample collection. Samples are collected every 24 hours followed by complete SIF exchange. The percentage of weight loss are calculated and compared using two-way ANOVA (Fisher's LSD method), with $p<0.05$ considered statistically significant.

HB-EGF release kinetics HB-EGF coated nanofiber scaffolds are cut into 0.5 cm length segments, completely submerged in 2 mL of DPBS solution in filter tubes (molecular weight cutoff 3,000), and incubated at 37° C. on a shaker. On days 1, 4, 7, 10, 14, 17 and 21, samples are transferred to new filter tubes and the supernatant in the original tube is spun down to concentrate HB-EGF, which were quantified by ELISA. Cumulative HB-EGF release are calculated and compared between different scaffolds using two-way ANOVA with Fisher's LSD method, with $p<0.05$ considered statistically significant.

HB-EGF Biopotency

To examine the biological activity of released HB-EGF, a cell proliferation assay are performed using NIH 3T3 cells. Briefly, 10,000 cells are added into each well of a 96-well plate in 150 pl of Assay Medium [(DMEM/F-12 containing 1% fetal bovine serum (FBS) and 0.5% bovine serum albumin (BSA)]. Released HB-EGF is diluted to a detectable range based on the concentration obtained by ELISA. Serial dilutions of the HB-EGF samples are prepared, with a total of 12 dilutions needed to establish standard curves. After 4 hours of culture, each cell-seeded well receive 100 pl of either released HB-EGF sample or standard. All samples are assayed in duplicate. After 48 hours, 5-bromo-2'-deoxyuridine (BrdU) incorporation is assessed to determine after compared with HB-EGF standard. Comparison of HB-EGF biopotency are conducted using Student's West, with $p<0.05$ considered statistically significant.

Example 4

Cell Seeding of the Nanofiber Scaffolds Biological Characterization of Nanofiber Scaffolds Isolation of Crypts, Smooth Muscle Cells, and Neural Stem Cells Crypts containing stem cells are isolated from 6-7 day old Lgr5-EGFP transgenic (TG) mice on a C57BL/6 background described in Chen et al. (*Lab. Invest.* 2012; 92:331-44), and are quantified using hemocytometry with Trypan blue. Lgr5-EGFP TG mice were used since these mice have been genetically engineered so that their native intestinal stem cells are fluorescently labeled (Barker et al., *Nature* 2007; 449:1003-7), which allows for tracking of the intestinal stem cells (ISC)s by fluorescent microscopy. Crypts are used immediately after isolation for in vitro characterization and in vivo intestine formation. Neural stem cells (NSCs) are isolated from fetal intestine at E11.5. Embryos are removed via C-section followed by harvesting of the intestines. Small and large bowel are dissected, minced and digested with collagenase (0.5 mg/ml) and dispase (0.5 mg/ml) for 60 minutes at 37° C. Cells will be triturated through a siliconized Pasteur pipette with the tip barely fore-polished. After filtration through 40 pm cell strainers, neural precursor cells are harvested by magnetic bead immunoselection using anti-P75 antibodies. NSCs are expanded in culture medium prior to in vitro characterization and in vivo intestine formation. SMCs are also harvested by magnetic bead immunoselection, but using anti-SMMHC antibodies. MSCs are expanded in culture medium prior to in vitro characterization and in vivo intestine formation.

Cell Seeding and Characterization

Crypts are encapsulated in pluronic F-127 hydrogel and then painted on the inner layer of nanofiber scaffolds. SMCs and NSCs are mixed in pluronic F-127 hydrogel followed by pressure infiltration into the scaffold from the outer surface. Both HB-EGF coated and non-coated scaffolds are seeded with cells and cultured in the customized dynamic bioreactor system that enables the dynamic culture of cell-scaffolds, which are used for ex vivo organ formation. At various time points, samples are observed microscopically and then fixed for SEM and histology. ISCs are detected by fluorescence microscopy. To ensure formation of all intestinal epithelial cell lineages, goblet cells are detected by alcian blue staining. Paneth cells are detected by lysozyme immunostaining, and enteroendocrine cells are detected by Chromogranin A immunostaining.

In the NSC cultures, colonies grow in size and formed neurospheres between days 1 to 21. Nestin immunostaining confirmed the presence of significant numbers of neuronal precursor cells in the neurospheres. The crypts are isolated and grown in ex vivo culture. In addition, amniotic fluid derived mesenchymal cells attached to the surface of a nanofiber scaffold.

Example 5

In Vivo Characterization of Engineered Intestine

In vivo characterization of HB-EGF-embedded nanofiber scaffolds of are conducted via anastomosis of the scaffold with native rat intestine in a defunctionalized Roux-en-Y intestinal limb, as described by Jwo et al. (Br J Surg. 2008; 95:657-63) with modifications. In this model, the mesentery are detached from a resected intestinal segment and used to wrap the cell-seeded scaffold for provision of blood supply after the scaffold has been anastomosed to the native intestine. Compared to published animal models, this model will provide a reliable blood supply for the engineered intestine.

Under general anesthesia, a midline laparotomy is performed on athymic nude rats (rnu/rnu) (n=12/group/time point) with a 3-5 cm incision, and the ligament of Treitz and ileocecal junction are identified. After dividing the proximal jejunum 10 cm from the ligament of Treitz, the Roux-en-Y bypass technique is used to make an end-to-side jejunoileostomy anastomosis with 8/0 nylon sutures between the proximal cut end and the side wall of the ileum, 20 cm away from the ileocecal junction. The distal cut end of the dysfunctional limb (Roux limb) is closed. A 1 mm silicon tube is inserted into the intestinal lumen and the other end of the tube is folded, tied, and buried in the right abdominal wall. A 10 cm central segment of the Roux limb is removed and substituted with a 2-cm scaffold tube anastomosed to native intestine with 8/0 nylon sutures The mesentery from the resected segment of intestine is wrapped around the scaffold tube as a source of blood supply to the implanted scaffold, and is immobilized with 8/0 silk sutures. Animals are radiographed at weeks 4 and 8 post-operatively, with contrast reagent given orally and via the tube buried in the right abdominal wall, and sacrificed immediately afterwards. Any signs of inflammation or adhesion formation are recorded during necropsy. The implant site with adjacent tissues are excised and fixed in 10% neutral buffered formalin, and processed for paraffin embedding. Tissue sections are evaluated for inflammation and tissue regeneration based on established grading scales, and scaffold degradation are assessed as well using Mann-Whitney U test, with $p<0.05$ considered statistically significant intestine.

Example 6

Cell Filtration System to Enrich Intestinal Stem Cells in Crypts

In the last decade, studies have focused on using organoid units (OU) as the cell source for TEL OU are cell clusters that are isolated from full-thickness intestine, and represent a mixed population of differentiated and undifferentiated cells. This cell source is not efficient for tissue regeneration because differentiated epithelial cells no longer have the capacity to proliferate, and will likely undergo apoptosis.

The present invention provides for a novel cell filtration system using multiple sieve membranes with different pore sizes. With one filtration step, different cell populations are obtained in a convenient and efficient cell recovery method from the removable sieve membrane. Use of donor intestine from an Lgr5 transgenic mice (which has fluorescent labeling of all intestinal stem cells (ISC)), allowed for the development of a custom-designed filtration system (FIGS. 8A-8D) to determine which filtration fraction is enriched in ISC. This system consists of a bottom filter, top cups, sieve membranes, and cell scraper (FIG. 8A). The smallest size (8 μm) has been loaded first and placed on the top of base filter cup (FIG. 8B). The second top cup has been placed on the base filter cup to secure the sieve membrane (FIG. 8C). Similarly, all other sizes of sieve membranes have been loaded in order from smaller to larger pore sizes, and a vacuum tube is connected.

Using the method set out in FIGS. 8A-8D, an optimal cell population between 8-70 μm was identified as highly enriched in fluorescently-labeled ISC (FIGS. 9A-9F). Fluorescently-labeled intestinal stem cells (ISC) appear first in the 50-70 μm population, increase in the 25-50 μm population, and disappear in the 8-25 μm and smaller populations. Based on these observations, an optimal cell population of 8-70 μm was selected for in vivo implantation studies as described in Example 7.

Figure 11:
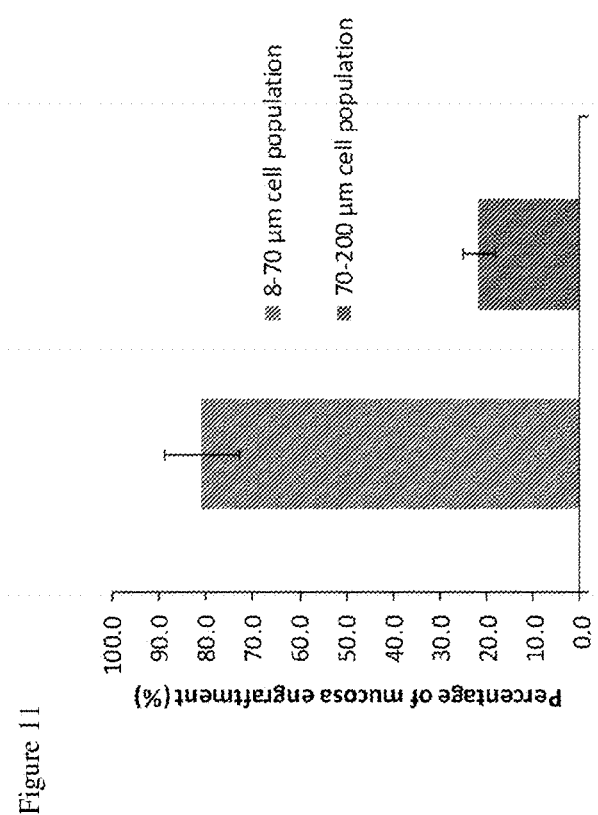
FIG. 11 depicts the effect of ISC-enriched cell seeding on mucosa production.

Briefly, the cells from Lewis rat pups were filtered with the filtration system, and two cell populations (8-70 μm and 70-200 μm) were seeded into PGA scaffolds and implanted into the peritoneal cavity of the dam rat by suturing to the undersurface of the abdominal wall. After 4 weeks of in vivo incubation, the samples were harvested and embedded in paraffin for Periodic acid-Schiff (PAS) staining (see FIG. 9). TEI formed from scaffolds seeded with the 8-70 μm cell population (enriched in ISC) showed a higher percentage of mucosal engraftment compared to TEI from scaffolds seeded with the 70-200 μm cell population (see FIG. 10) The percent of mucosal engraftment from scaffolds seeded with the 8-70 μm cell population is significantly higher than that from the 70-200 μm cell population (p<0.01). Five sections were measured at 200 μm intervals from each sample and 12 samples were measured from each cell population (see FIG. 11)

To confirm the sizes of the enriched intestinal stem cells, frozen tissue sections from Lgr5EGFP mice was mounted onto glass slide with VectaShield medium containing DAPI. This staining verified that intestinal stem cells reside in crypts underneath villi. The length of villi and crypts was measured using Zeiss LSM image browser (Version 4.2.0.121). Scale bar. Exemplary measurements are provided in Table 3.

TABLE 3

Representative measure of villi and crypts length[1]

|  | Villi Length(μm) | Crypts Length (μm) |
|---|---|---|
|  | 91.69 | 33.75 |
|  | 177.00 | 28.79 |
|  | 176.70 | 28.73 |
|  | 96.99 | 44.20 |
| Mean | 135.60 | 33.87 |
| STDEV | 47.69 | 7.28 |

Example 7

HB-EGF Incorporation into PGA Enhances the Formation of Tissue Engineered Intestine Preparation of PGA scaffolds were prepared as described in Example 2. Briefly, tubular PGA scaffolds were prepared with PGA BioFelt (Biomedical Structures, thickness=1 mm, density=60 mg/ml) and hydrated with or without HB-EGF (0, 1 or 10 μg in 100 μl PBS). Select scaffolds were subjected to subsequent $CO_2$ infusion (900 psi) for 1 h to increase HB-EGF incorporation.

Figure 12:
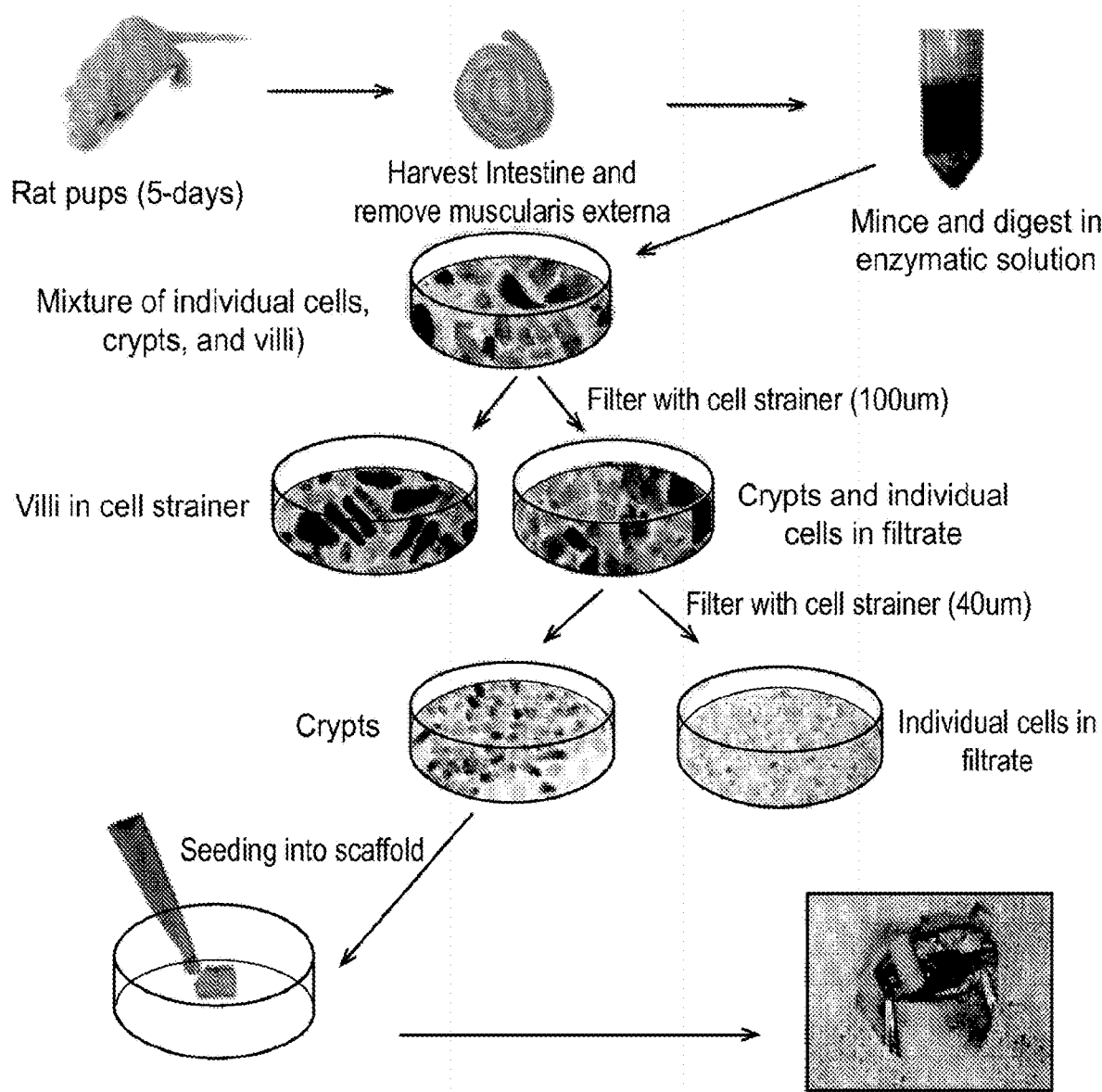
FIG. 12 depicts the scheme used to seed cells in the PGA scaffolds.

Small intestines were harvested from Lewis rat pups, minced, and digested in dispase and collagenase for 30 minutes. Intestinal stem cell (ISC) enriched crypts were obtained by filtration with 100 μm and 40 μm cell strainers. Scaffolds (1 cm length) were then seeded with 1.5-2 million crypts and implanted into the peritoneal cavity of the dam of the donor rat pups, on the interior surface of the abdominal wall. After 4 weeks of in vivo incubation, explants were assessed histologically and villous length measured as described in Example 1 and depicted in FIG. 12.

Figure 13:
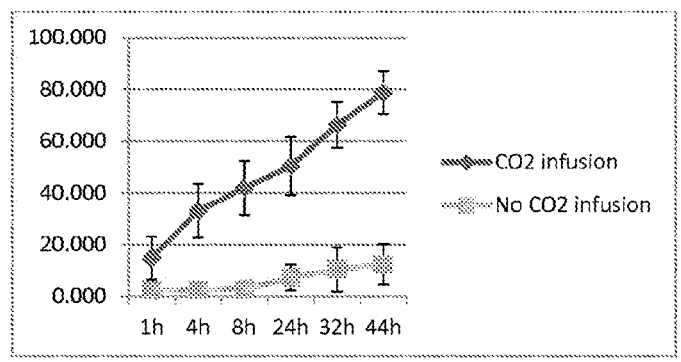
FIG. 13 depicts the HB-EGF release kinetics from the PGA scaffolds.
Figure 14:
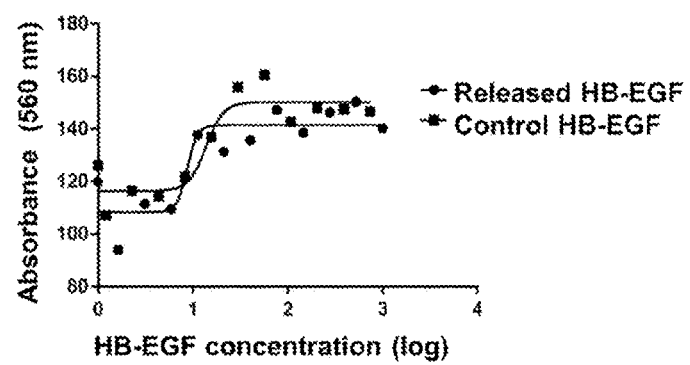
FIG. 14 depicts the biopotency of the HB-EGF released from the PGA scaffold.

As shown in FIG. 13, HB-EGF release kinetic studies were assessed using an HB-EGF ELISA. Increased amounts of HB-EGF were released from PGA scaffolds with $CO_2$ infusion compared to those without $CO_2$ infusion. The biopotency of HB-EGF released from scaffolds was assessed using a cell proliferation assay, and was very similar to that of control HB-EGF, as confirmed by an EC50 fitting curve (Graphpad Prism 6 software) (p=0.209; see FIG. 14)

Figure 15:
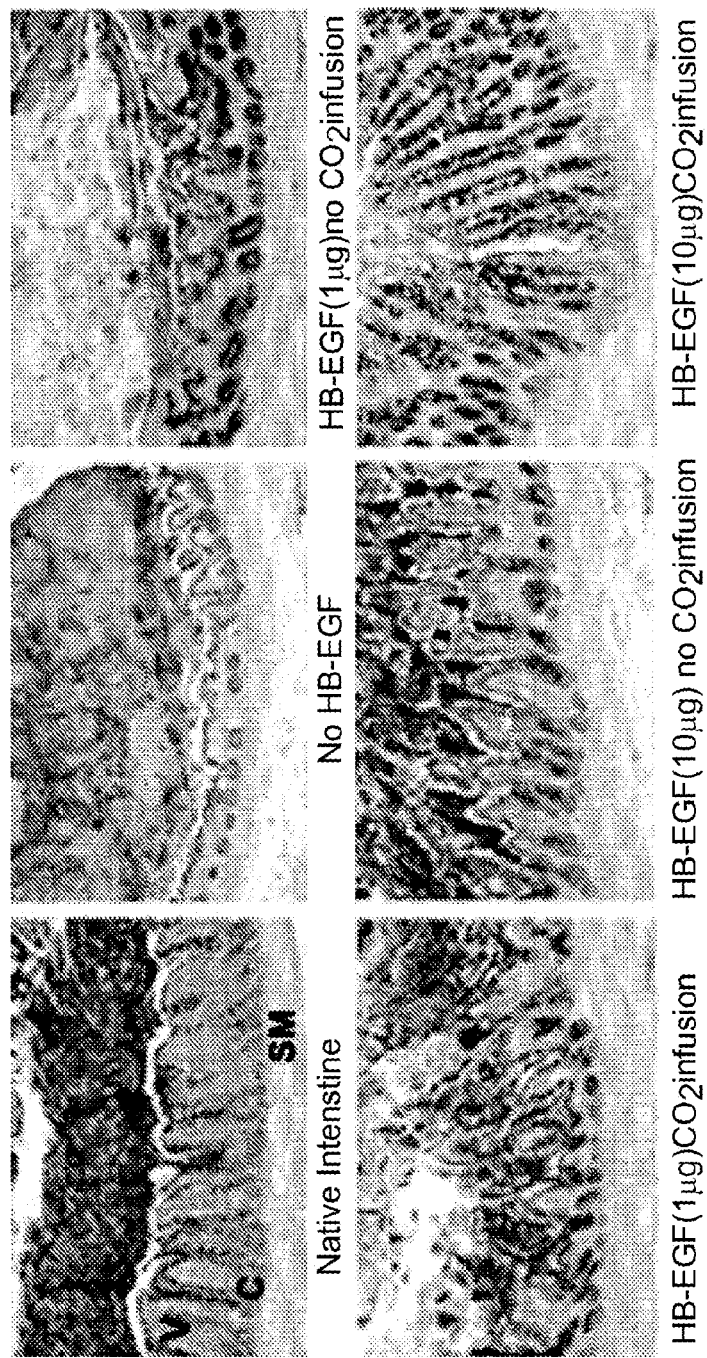
FIG. 15 depicts the histology of the native intestine compared to the TEI of the invention. TEI produced from in vivo incubation of crypt-seeded scaffolds (panels b-f) was histologically very similar to that of native intestine (panel a). PAS staining, V=villi, C=crypts, SM=smooth muscle, scale bar=200 μm
Figure 16:
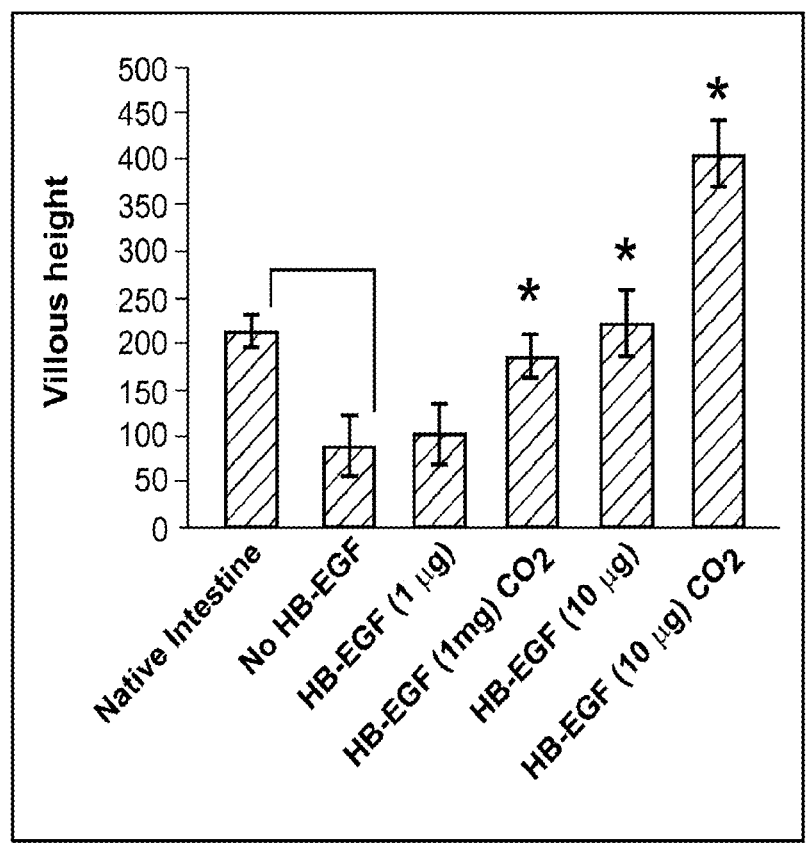
FIG. 16 depicts the villous height of native intestine compared to the TEI of the invention. HB-EGF infusion of scaffolds led to TEI with increased villous height. The villous height of native intestine was 212.9±16.8 μm. no HB-EGF 88.7±32.3 μm; HB-EGF (1 μg) 101.8±32.5 μm; HB-EGF (1 μg)+$CO_2$ infusion 186.0±23.4 μm; HB-EGF (10 μg) 222.6±34.6 μm; HB-EGF (10 μg)+$CO_2$ infusion 406.34±37 μm.

Histology was carried out on native intestine and compared to TEI and depicted in FIG. 15. TEI produced from in vivo incubation of crypt-seeded scaffolds was histologically very similar to that of native intestine. HB-EGF infusion of scaffolds led to TEI with increased villous height, increased crypt numbers, and well-developed smooth muscle layers. In addition, villious height of the native intestine was compared with the TEI.HB-EGF infusion of scaffolds led to TEI with increased villous height. The villous height of native intestine was 212.9±16.8 μm. The villous height of TEI increased with increasing concentrations of HB-EGF and with the use of $CO_2$ infusion as shown in FIG. 16.

These experiments demonstrate that HB-EGF incorporation into scaffolds improves the quality of the TEI produced. In addition, $CO_2$ infusion improves the efficacy of HB-EGF incorporation into TEI scaffolds. The use of HB-EGF in the production of TEI may be beneficial for the future treatment of patients with short bowel syndrome.

What is claimed:

1. An engineered intestine construct comprising a nanofiber scaffold seeded with neural stem cells, smooth muscle cells and intestinal stem cells from intestinal crypts, and wherein the nanofiber scaffold comprises HB-EGF polypeptide or a fragment thereof.

2. An engineered intestine construct comprising a nanofiber scaffold seeded with neural stem cells, smooth muscle cells and intestinal stem cells from intestinal crypts, wherein at least one of the neural stem cells, smooth muscle cells or intestinal stem cells overexpress HB-EGF polypeptide or a fragment thereof.

3. An engineered intestine construct comprising a multilayer nanofiber scaffold,
    wherein the multilayer nanofiber scaffold comprises at least an inner layer and an outer layer,
    wherein the outer layer comprises neural stem cells and smooth muscle cells, and
    wherein the inner layer comprises intestinal stem cells.

4. The engineered intestine construct of claim 3 wherein at least one of the layers comprises HB-EGF polypeptide or a fragment.

5. The engineered intestine construct of claim 3 wherein the construct further comprises at least one middle layer.

6. The engineered intestine construct of claim 1 wherein the nanofiber scaffold comprises Poly (glycolic acid) (PGA) nanofibers, Poly (ε-caprolactone) (PCL) nanofibers, Poly (-caprolactone-co-lactic acid) (PLC) nanofibers, Poly (L-lactic acid) (PLLA) nanofibers, Poly (D-lactic acid-co-glycolic acid) (PDLGA) nanofibers, Poly (D-lactic acid-co-glycolic acid) (PLGA) nanofibers, Polyurethane (PU) nanofibers, Polydioxanone (PDO) nanofibers or a combination thereof.

7. The engineered intestine construct of claim 1 wherein the construct comprises a layer of macrofibers between two layers.

8. The engineered intestine construct of claim 7 where the layer of macrofibers comprises PGA.

* * * * *

SEQUENCE LISTING

<160> NUMBER OF SEQ ID NOS: 2

<210> SEQ ID NO 1
<211> LENGTH: 624
<212> TYPE: DNA
<213> ORGANISM: Homo sapiens
<220> FEATURE:
<221> NAME/KEY: CDS
<222> LOCATION: (1)..(624)

<400> SEQUENCE: 1

```
atg aag ctg ctg ccg tcg gtg gtg ctg aag ctc ttt ctg gct gca gtt        48
Met Lys Leu Leu Pro Ser Val Val Leu Lys Leu Phe Leu Ala Ala Val
1               5                   10                  15 ctc tcg gca ctg gtg act ggc gag agc ctg gag cgg ctt cgg aga ggg        96
Leu Ser Ala Leu Val Thr Gly Glu Ser Leu Glu Arg Leu Arg Arg Gly
                20                  25                  30 cta gct gct gga acc agc aac ccg gac cct ccc act gta tcc acg gac        144
Leu Ala Ala Gly Thr Ser Asn Pro Asp Pro Pro Thr Val Ser Thr Asp
            35                  40                  45 cag ctg cta ccc cta gga ggc ggc cgg gac cgg aaa gtc cgt gac ttg        192
Gln Leu Leu Pro Leu Gly Gly Gly Arg Asp Arg Lys Val Arg Asp Leu
        50                  55                  60 caa gag gca gat ctg gac ctt ttg aga gtc act tta tcc tcc aag cca        240
Gln Glu Ala Asp Leu Asp Leu Leu Arg Val Thr Leu Ser Ser Lys Pro
65                  70                  75                  80
```

```
caa gca ctg gcc aca cca aac aag gag gag cac ggg aaa aga aag aag      288
Gln Ala Leu Ala Thr Pro Asn Lys Glu Glu His Gly Lys Arg Lys Lys
                85                  90                  95 aaa ggc aag ggg cta ggg aag aag agg gac cca tgt ctt cgg aaa tac      336
Lys Gly Lys Gly Leu Gly Lys Lys Arg Asp Pro Cys Leu Arg Lys Tyr
100                 105                 110 aag gac ttc tgc atc cat gga gaa tgc aaa tat gtg aag gag ctc cgg      384
Lys Asp Phe Cys Ile His Gly Glu Cys Lys Tyr Val Lys Glu Leu Arg
            115                 120                 125 gct ccc tcc tgc atc tgc cac ccg ggt tac cat gga gag agg tgt cat      432
Ala Pro Ser Cys Ile Cys His Pro Gly Tyr His Gly Glu Arg Cys His
        130                 135                 140 ggg ctg agc ctc cca gtg gaa aat cgc tta tat acc tat gac cac aca      480
Gly Leu Ser Leu Pro Val Glu Asn Arg Leu Tyr Thr Tyr Asp His Thr
145                 150                 155                 160 acc atc ctg gcc gtg gtg gct gtg gtg ctg tca tct gtc tgt ctg ctg      528
Thr Ile Leu Ala Val Val Ala Val Val Leu Ser Ser Val Cys Leu Leu
                165                 170                 175 gtc atc gtg ggg ctt ctc atg ttt agg tac cat agg aga gga ggt tat      576
Val Ile Val Gly Leu Leu Met Phe Arg Tyr His Arg Arg Gly Gly Tyr
            180                 185                 190 gat gtg gaa aat gaa gag aaa gtg aag ttg ggc atg act aat tcc cac      624
Asp Val Glu Asn Glu Glu Lys Val Lys Leu Gly Met Thr Asn Ser His
        195                 200                 205

<210> SEQ ID NO 2
<211> LENGTH: 208
<212> TYPE: PRT
<213> ORGANISM: Homo sapiens

<400> SEQUENCE: 2

Met Lys Leu Leu Pro Ser Val Val Leu Lys Leu Phe Leu Ala Ala Val
1               5                   10                  15

Leu Ser Ala Leu Val Thr Gly Glu Ser Leu Glu Arg Leu Arg Arg Gly
            20                  25                  30

Leu Ala Ala Gly Thr Ser Asn Pro Asp Pro Thr Val Ser Thr Asp
        35                  40                  45

Gln Leu Leu Pro Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Asn Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190
```

```
Asp Val Glu Asn Glu Glu Lys Val Lys Leu Gly Met Thr Asn Ser His
        195                 200                 205
```